(12) United States Patent
Yanagawa et al.

(10) Patent No.: US 9,487,457 B2
(45) Date of Patent: Nov. 8, 2016

(54) METHOD FOR PRODUCING MONOCYCLIC AROMATIC HYDROCARBONS

(75) Inventors: Shinichiro Yanagawa, Tokyo (JP); Yasuyuki Iwasa, Tokyo (JP); Ryoji Ida, Tokyo (JP); Masahide Kobayashi, Tokyo (JP); Susumu Yasui, Yokohama (JP); Yoshishige Sugi, Yokohama (JP); Atsushi Fukui, Yokohama (JP); Akira Utatsu, Yokohama (JP)

(73) Assignees: JX Nippon Oil & Energy Corporation, Tokyo (JP); CHIYODA CORPORATION, Yokohama-shi, Kanagawa (JP)

( * ) Notice: Subject to any disclaimer, the term of this patent is extended or adjusted under 35 U.S.C. 154(b) by 288 days.

(21) Appl. No.: 14/119,576

(22) PCT Filed: May 24, 2012

(86) PCT No.: PCT/JP2012/063351
§ 371 (c)(1),
(2), (4) Date: Feb. 7, 2014

(87) PCT Pub. No.: WO2012/161264
PCT Pub. Date: Nov. 29, 2012

(65) Prior Publication Data
US 2014/0200377 A1    Jul. 17, 2014

(30) Foreign Application Priority Data
May 24, 2011   (JP) .................. 2011-115643

(51) Int. Cl.
*C07C 2/42*     (2006.01)
*C07C 2/76*     (2006.01)
(Continued)

(52) U.S. Cl.
CPC . *C07C 5/02* (2013.01); *C07C 4/02* (2013.01); *C07C 6/126* (2013.01); *C07C 7/00* (2013.01);
(Continued)

(58) Field of Classification Search
CPC .............. C07C 2/42; C07C 2/76; C07C 5/11; C07C 57/00

USPC ....... 585/319, 418, 266, 268; 208/67, 62, 49
See application file for complete search history.

(56) References Cited

U.S. PATENT DOCUMENTS

| | | | |
|---|---|---|---|
| 3,242,222 | A | 3/1966 | Ryan |
| 3,772,184 | A | 11/1973 | Bertolacini et al. |

(Continued)

FOREIGN PATENT DOCUMENTS

| | | |
|---|---|---|
| EP | 0035194 A1 | 9/1981 |
| JP | H03-2128 A | 1/1991 |

(Continued)

OTHER PUBLICATIONS

Int'l Search Report issued Aug. 28, 2012 in Int'l Application No. PCT/JP2012/063351.

(Continued)

*Primary Examiner* — Thuan D Dang
(74) *Attorney, Agent, or Firm* — Panitch Schwarze Belisario & Nadel LLP

(57) ABSTRACT

The present method for producing monocyclic aromatic hydrocarbons is a method for producing monocyclic aromatic hydrocarbons having 6 to 8 carbon atoms. This method includes a cracking and reforming reaction step of bringing oil feedstock into contact with a catalyst to cause a reaction and obtain a product containing monocyclic aromatic hydrocarbons having 6 to 8 carbon atoms and a heavy fraction having 9 or more carbon atoms, a purification and recovery step of purifying and recovering the monocyclic aromatic hydrocarbons having 6 to 8 carbon atoms separated from the product formed by the cracking and reforming reaction step, and a first returning step of returning at least a portion of toluene obtained by the purification and recovery step to the cracking and reforming reaction step.

12 Claims, 4 Drawing Sheets

(51) Int. Cl.
*C07C 5/11* (2006.01)
*C07C 57/00* (2006.01)
*C07C 5/02* (2006.01)
*C10G 11/05* (2006.01)
*C07C 6/12* (2006.01)
*C10G 11/18* (2006.01)
*C07C 4/02* (2006.01)
*C07C 7/00* (2006.01)
*C10G 35/095* (2006.01)
*C10G 45/44* (2006.01)
*C10G 35/04* (2006.01)
*C10G 35/06* (2006.01)
*C10G 35/10* (2006.01)
*B01J 23/44* (2006.01)
*B01J 23/755* (2006.01)
*B01J 23/883* (2006.01)
*B01J 23/888* (2006.01)
*B01J 29/40* (2006.01)

(52) U.S. Cl.
CPC ............... *C10G 11/05* (2013.01); *C10G 11/18* (2013.01); *C10G 35/04* (2013.01); *C10G 35/065* (2013.01); *C10G 35/095* (2013.01); *C10G 35/10* (2013.01); *C10G 45/44* (2013.01); *B01J 23/44* (2013.01); *B01J 23/755* (2013.01); *B01J 23/883* (2013.01); *B01J 23/888* (2013.01); *B01J 29/405* (2013.01); *C10G 2300/1044* (2013.01); *C10G 2300/1048* (2013.01); *C10G 2300/301* (2013.01); *C10G 2300/4081* (2013.01); *C10G 2400/20* (2013.01); *C10G 2400/30* (2013.01); *Y02P 20/132* (2015.11)

(56) References Cited

U.S. PATENT DOCUMENTS

| | | | |
|---|---|---|---|
| 4,053,388 A | 10/1977 | Bailey | |
| 8,912,377 B2* | 12/2014 | Kim | C10G 11/02 585/256 |
| 2002/0091060 A1* | 7/2002 | Cheng | B01J 29/061 502/63 |
| 2004/0215042 A1* | 10/2004 | Bottcher | C07C 5/10 585/400 |

FOREIGN PATENT DOCUMENTS

| | | |
|---|---|---|
| JP | H03-26791 A | 2/1991 |
| JP | H03-52993 A | 3/1991 |
| JP | H04-222634 A | 8/1992 |
| JP | H10-513498 A | 12/1998 |
| JP | H11-57481 A | 3/1999 |
| JP | 2004-137353 A | 5/2004 |
| JP | 2007-154151 A | 6/2007 |
| JP | 2010-532752 A | 10/2010 |
| WO | 9624568 A1 | 8/1996 |
| WO | 2005075389 A1 | 8/2005 |
| WO | 2009008876 A1 | 1/2009 |

OTHER PUBLICATIONS

Extended European Search Report issued Oct. 7, 2014 in EP Application No. 12790261.7.

Office Action issued Feb. 10, 2015 in JP Application No. 2011-115643.

Office Action issued on May 24, 2016 in EP Application No. 12790261.7.

* cited by examiner

METHOD FOR PRODUCING MONOCYCLIC AROMATIC HYDROCARBONS

CROSS-REFERENCE TO RELATED APPLICATION

This application is a Section 371 of International Application No. PCT/JP2012/063351, filed Mar. 15, 2012, which was published in the Japanese language on Nov. 29, 2012, under International Publication No. WO 2012/161264 A1, and the disclosure of which is incorporated herein by reference.

TECHNICAL FIELD

The present invention relates to a method for producing monocyclic aromatic hydrocarbons.
Priority is claimed on Japanese Patent Application No. 2011-115643, filed May 24, 2011, the content of which is incorporated herein by reference.

BACKGROUND ART

Light cycle oil (hereinafter, called "LCO"), which is cracked diesel oil produced using a fluid catalytic cracking (hereinafter, called "FCC") unit, contains a large amount of polycyclic aromatic hydrocarbons, and has been utilized as diesel oil or fuel oil. However, in recent years, investigations have been conducted to obtain high value-added monocyclic aromatic hydrocarbons having 6 to 8 carbon atoms (for example, benzene, toluene, xylene, ethylbenzene and the like) that can be utilized as high-octane gasoline base materials or petrochemical starting materials, from the LCO.

For example, Patent Documents 1 to 3 suggest methods for producing a monocyclic aromatic hydrocarbon from polycyclic aromatic hydrocarbons that are contained in a large amount in LCO or the like, by using a zeolite catalyst.

CITATION LIST

Patent Document

Patent Document 1: Japanese Unexamined Patent Application, First Publication No. H3-2128
Patent Document 2: Japanese Unexamined Patent Application, First Publication No. H3-52993
Patent Document 3: Japanese Unexamined Patent Application, First Publication No. H3-26791

SUMMARY OF INVENTION

Technical Problem

However, with the methods disclosed in Patent Documents 1 to 3, the yield of monocyclic aromatic hydrocarbons having 6 to 8 carbon atoms is not sufficiently improved.

Moreover, even though benzene, toluene, and xylene as monocyclic aromatic hydrocarbons having 6 to 8 carbon atoms are products of a high value, the demand for benzene or xylene has become higher than that for toluene, depending on the circumstances of the market. In this case, as monocyclic aromatic hydrocarbons having 6 to 8 carbon atoms, it is particularly preferable to produce benzene and xylene at a yield higher than that of toluene. However, conventionally, a process for selectively producing benzene or xylene at a yield relatively higher than that of toluene has not been provided.

The present invention has been made in consideration of the above circumstances, and an object thereof is to provide a method for producing monocyclic aromatic hydrocarbons that makes it possible to produce monocyclic aromatic hydrocarbons having 6 to 8 carbon atoms at a high yield from oil feedstock containing polycyclic aromatic hydrocarbon and to produce benzene or xylene at a yield higher than that of toluene.

Solution to Problem

The method for producing monocyclic aromatic hydrocarbons according to a first embodiment of the present invention is a method for producing monocyclic aromatic hydrocarbons having 6 to 8 carbon atoms from oil feedstock having a 10 vol % distillation temperature of 140° C. or higher and a 90 vol % distillation temperature of 380° C. or lower, and includes:

a cracking and reforming reaction step of bringing the oil feedstock into contact with a catalyst for producing monocyclic aromatic hydrocarbons containing a crystalline aluminosilicate to cause a reaction and obtain a product containing monocyclic aromatic hydrocarbons having 6 to 8 carbon atoms and a heavy fraction having 9 or more carbon atoms, a purification and recovery step of purifying and recovering the monocyclic aromatic hydrocarbons having 6 to 8 carbon atoms separated from the product formed by the cracking and reforming reaction step, and a first returning step of returning at least a portion of toluene obtained by the purification and recovery step to the cracking and reforming reaction step.

A method for producing monocyclic aromatic hydrocarbons according to a second embodiment of the present invention is preferably the method for producing monocyclic aromatic hydrocarbons according to the first embodiment that further includes a second returning step of returning the heavy fraction having 9 or more carbon atoms separated from the product formed by the cracking and reforming reaction step to the cracking and reforming reaction step.

A method for producing monocyclic aromatic hydrocarbons according to a third embodiment of the present invention is preferably the method for producing monocyclic aromatic hydrocarbons according to the first or second embodiment that further includes a hydrogenation reaction step of hydrogenating the heavy fraction having 9 or more carbon atoms separated from the product formed by the cracking and reforming reaction step, and a recycle step of returning hydrogenation products of the heavy fraction obtained by the hydrogenation reaction step to the cracking and reforming reaction step.

A method for producing monocyclic aromatic hydrocarbons according to a fourth embodiment of the present invention is preferably the method for producing monocyclic aromatic hydrocarbons according to the third embodiment, in which the first returning step is a step of supplying the toluene to a middle portion of a hydrogenation reactor used in the hydrogenation reaction step.

A method for producing monocyclic aromatic hydrocarbons according to a fifth embodiment of the present invention is preferably the method for producing monocyclic aromatic hydrocarbons according to the third or fourth embodiment that further includes, between the cracking and reforming reaction step and the hydrogenation reaction step, a dilution step of adding a diluent formed of a hydrocarbon to the heavy fraction having 9 or more carbon atoms separated from the product formed by the cracking and reforming reaction step.

A method for producing monocyclic aromatic hydrocarbons according to a sixth embodiment of the present invention is preferably the method for producing monocyclic aromatic hydrocarbons according to the fifth embodiment, in which as the diluent, at least a portion of toluene obtained by the purification and recovery step is used.

A method for producing monocyclic aromatic hydrocarbons according to a seventh embodiment of the present invention is preferably the method for producing monocyclic aromatic hydrocarbons according to the fifth embodiment that further includes, after the hydrogenation reaction step, a diluent recovering step of separating and removing the diluent from the hydrogenation products obtained by the hydrogenation reaction step and recovering the diluent to reuse it as the diluent of the dilution step.

Advantageous Effects of Invention

According to the method for producing monocyclic aromatic hydrocarbons of the present invention, monocyclic aromatic hydrocarbons having 6 to 8 carbon atoms can be produced at a high yield from oil feedstock containing polycyclic aromatic hydrocarbons.

Moreover, since the method includes the first returning step of returning at least a portion of toluene obtained by the purification and recovery step to the cracking and reforming reaction step, by causing a reaction such as disproportionation of toluene in the cracking and reforming reaction step, benzene and xylene can be obtained from the toluene. Accordingly, when the demand for benzene or xylene is relatively higher than that for toluene, benzene or xylene can be selectively produced at a yield higher than that of toluene.

DESCRIPTION OF EMBODIMENTS

[First Embodiment]

Hereinafter, a first embodiment of the method for producing monocyclic aromatic hydrocarbons of the present invention will be described.

Figure 1:
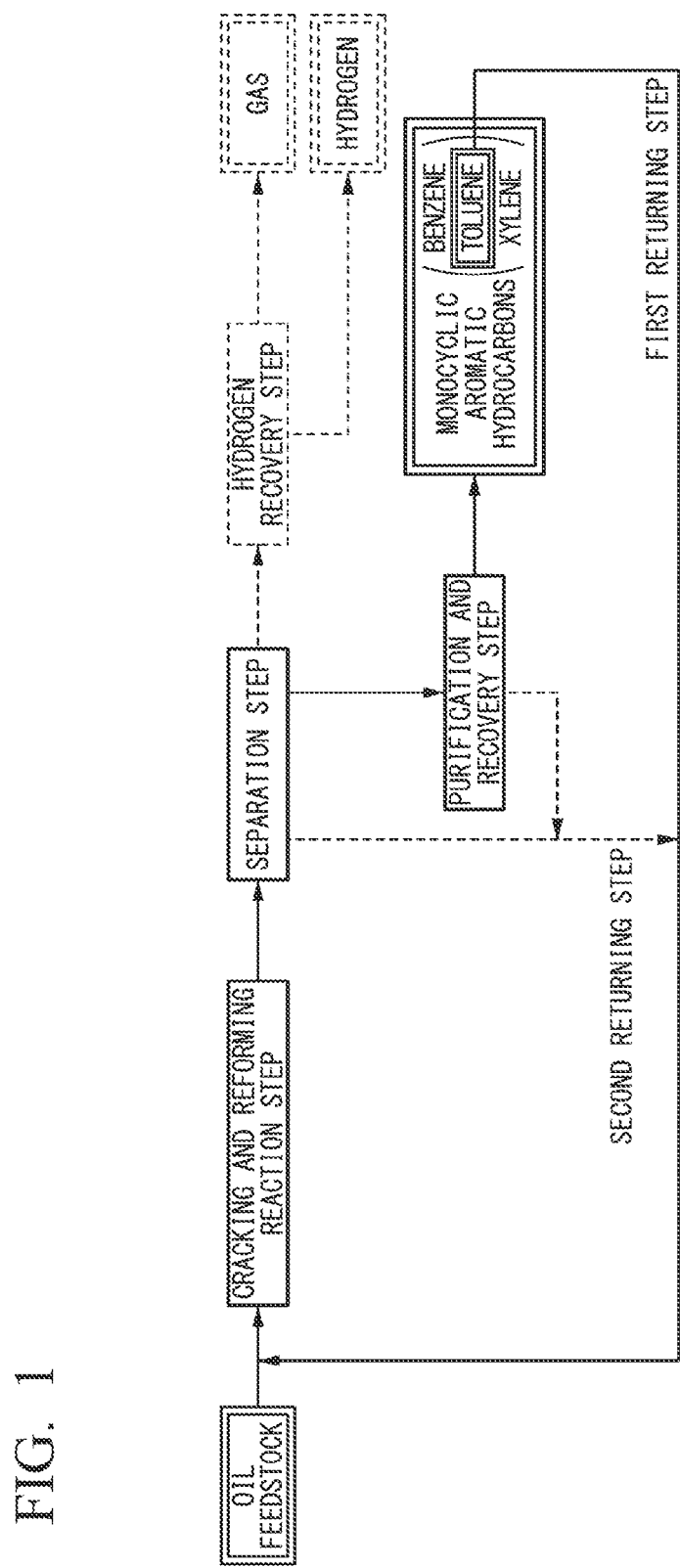
FIG. 1 is a view for illustrating a first embodiment of the method for producing monocyclic aromatic hydrocarbons of the present invention.

FIG. 1 is a view for illustrating the first embodiment of the method for producing monocyclic aromatic hydrocarbons of the present invention. The method for producing monocyclic aromatic hydrocarbons of the present embodiment is a method for producing monocyclic aromatic hydrocarbons having 6 to 8 carbon atoms from oil feedstock.

That is, the method for producing monocyclic aromatic hydrocarbons of the present embodiment may include the respective steps shown in FIG. 1.

(1) A cracking and reforming reaction step of bringing oil feedstock into contact with a catalyst for producing monocyclic aromatic hydrocarbons to cause a reaction and obtain monocyclic aromatic hydrocarbons having 6 to 8 carbon atoms and a heavy fraction having 9 or more carbon atoms (2) A separation step of separating a product formed by the cracking and reforming reaction step into plural fractions (3) A purification and recovery step of purifying and recovering monocyclic aromatic hydrocarbons separated by the separation step (4) A first returning step of returning at least a portion of toluene obtained by the purification and recovery step to the cracking and reforming reaction step (5) A second returning step of returning the heavy fraction having 9 or more carbon atoms separated from the product formed by the cracking and reforming reaction step to the cracking and reforming reaction step (6) A hydrogen recovery step of recovering hydrogen produced as a by-product by the cracking and reforming reaction step, from a gas component separated by the separation step Among the steps (1) to (6), the steps (1), (3), and (4) are steps included in the first embodiment, the steps (2), (5), and (6) are optional steps, and the step (5) is included in a second embodiment.

Hereinafter, the respective steps will be described in detail.

<Cracking and Reforming Reaction Step>

In the cracking and reforming reaction step, oil feedstock is brought into contact with a catalyst for producing monocyclic aromatic hydrocarbons to partially hydrogenate the polycyclic aromatic hydrocarbons by a reaction in which hydrogen is transferred from a saturated hydrocarbons which is contained in the oil feedstock and is used as a hydrogen-donating source. As a result, the polycyclic aromatic hydrocarbons are converted into monocyclic aromatic hydrocarbons by ring-opening. Moreover, by cyclization and dehydrogenation of the saturated hydrocarbons contained in the oil feedstock or obtained in the cracking process, the polycyclic aromatic hydrocarbons can also be converted into monocyclic aromatic hydrocarbons. In addition, by cracking the monocyclic aromatic hydrocarbons having 9 or more carbon atoms, monocyclic aromatic hydrocarbons having 6 to 8 carbon atoms can also be obtained. As a result, a product containing monocyclic aromatic hydrocarbons having 6 to 8 carbon atoms and a heavy fraction having 9 or more carbon atoms are obtained. Furthermore, as will be described later, at least a portion of toluene is returned to the cracking and reforming reaction step by the first returning step. When the toluene is brought into contact with the catalyst for producing monocyclic aromatic hydrocarbons, reactions such as disproportionation, transalkylation, and demethylation occur. In this manner, benzene and xylene are produced from toluene.

In addition, if a portion of the toluene having undergone the first returning step is supplied to a step which is different from the cracking and reforming reaction step of converting the toluene into benzene, xylene, and the like, and the converted product is recycled in the purification and recovery step, the yield of benzene and xylene can be increased among monocyclic aromatic hydrocarbons.

Moreover, the product contains, in addition to the monocyclic aromatic hydrocarbons or the heavy fraction, hydrogen, methane, ethane, ethylene, LPG (propane, propylene, butane, and butene), and the like. The heavy fraction contains a large amount of bicyclic aromatic hydrocarbons such as naphthalene, methylnaphthalene, and dimethylnaphthalene. Further, depending on the type of oil feedstock, the heavy fraction also contains aromatic hydrocarbon having three or more rings, such as anthracene. In the present application, the bicyclic aromatic hydrocarbons and the aromatic hydrocarbons having three or more rings are collectively called polycyclic aromatic hydrocarbons.

In the cracking and reforming reaction step, most of the components such as naphthenobenzenes, paraffins, and naphthenes in the oil feedstock are decreased by the production of monocyclic aromatic hydrocarbons. Moreover, a portion of polycyclic aromatic hydrocarbons is converted into monocyclic aromatic hydrocarbons by cracking and hydrogen transfer along with saturated hydrocarbons, but at the same time, the chain thereof at the alkyl side is cut, whereby bicyclic aromatic hydrocarbons having a small number of side chains, such as naphthalene, methylnaphthalene, and dimethylnaphthalene are also produced as a by-product. Accordingly, in the cracking and reforming reaction step, monocyclic aromatic hydrocarbons are produced at a high yield, and at the same time, bicyclic aromatic hydrocarbons are also produced as a heavy fraction having 9 or more carbon atoms, as a by-product.

(Oil Feedstock)

The oil feedstock used in the present embodiment is oil having a 10 vol % distillation temperature of 140° C. or higher and a 90 vol % distillation temperature of 380° C. or lower. If oil having a 10 vol % distillation temperature of lower than 140° C. is used, monocyclic aromatic hydrocarbons are produced from light oil, and this does not correspond to the gist of the present embodiment. If oil having a 90 vol % distillation temperature exceeding 380° C. is used, the yield of monocyclic aromatic hydrocarbons decreases, and the amount of coke deposited onto the catalyst for producing monocyclic aromatic hydrocarbons increases, whereby a degree of the catalytic activity tends to rapidly decrease.

The 10 vol % distillation temperature of the oil feedstock is preferably 150° C. or higher, and the 90 vol % distillation temperature of the oil feedstock is preferably 360° C. or lower.

The 10 vol % distillation temperature and 90 vol % distillation temperature mentioned herein refer to values measured based on JIS K 2254 "Petroleum products—Distillation Testing Method".

Examples of the oil feedstock having a 10 vol % distillation temperature of 140° C. or higher and a 90 vol % distillation temperature of 380° C. or lower include LCO, hydrogenation purified oil of LCO, coal liquefaction oil, heavy oil hydrocracking purified oil, straight run kerosene, straight run gas oil, coker kerosene, coker gas oil, oil sand hydrocracking purified oil, and the like.

A polycyclic aromatic hydrocarbon is a compound that has low reactivity and is not easily converted into a monocyclic aromatic hydrocarbon by the cracking and reforming reaction step of the present embodiment. On the other hand, when being hydrogenated by the hydrogenation reaction step in the second embodiment which will be described later, the polycyclic aromatic hydrocarbon is converted into naphthenobenzenes and recycled by being supplied to the cracking and reforming reaction step. In this way, the polycyclic aromatic hydrocarbon can be converted into a monocyclic aromatic hydrocarbon. Accordingly, the content of the polycyclic aromatic hydrocarbons in the oil feedstock is not particularly limited even if the content is large. However, among polycyclic aromatic hydrocarbons, aromatic hydrocarbons having three or more rings consume a large amount of hydrogen in the hydrogenation reaction step. Furthermore, the hydrogenation products of the aromatic hydrocarbons having three or more rings exhibit low reactivity in the cracking and reforming reaction step. Therefore, it is not preferable for the oil feedstock to contain a large amount of the polycyclic aromatic hydrocarbons having three or more rings. Consequently, the content of the aromatic hydrocarbons having three or more rings in the oil feedstock is preferably 25 vol % or less and more preferably 15 vol % or less.

As oil feedstock that contains bicyclic aromatic hydrocarbons converted into naphthenobenzene in the hydrogenation reaction step and the reduced amount of the aromatic hydrocarbons having three or more rings, for example, oil feedstock having a 90 vol % distillation temperature of 330° C. or lower is more preferable.

The polycyclic aromatic hydrocarbons mentioned herein mean the sum of the content of bicyclic aromatic hydrocarbons (bicyclic aromatic fraction) and the content of aromatic hydrocarbons having three or more rings (aromatic fraction having three or more rings) that is measured based on JPI-5S-49 "Petroleum products—Hydrocarbon type test methods—High performance liquid chromatography method" or analyzed by FID gas chromatography or 2-dimensional gas chromatography. Hereinafter, when the content of the polycyclic aromatic hydrocarbons, the bicyclic aromatic hydrocarbons, and the aromatic hydrocarbons having three or more rings is expressed by vol %, this shows that the content is measured based on JPI-5S-49, and when it is expressed by mass %, this shows that the content is measure based on FID gas chromatography or 2-dimensional gas chromatography.

(Reaction Type)

Examples of the reaction type at the time when the oil feedstock is brought into contact with a catalyst for producing monocyclic aromatic hydrocarbons to cause a reaction include a fixed bed, a moving bed, a fluidized bed, and the like. Since the present embodiment uses a heavy fraction as a feedstock, it is preferable to use a fluidized bed which makes it possible to continuously remove a coke fraction attached to the catalyst and to stably perform the reaction. Moreover, it is particularly preferable to use a continuous regeneration type fluidized bed in which a catalyst circulates between a reactor and a regenerator to make it possible to continuously repeat the reaction and regeneration. The fluidized bed generally includes a bed cracking type and a riser cracking type. In the present embodiment, it is desirable to perform the reaction under mild conditions by using a bed cracking type. The oil feedstock to be brought into contact with the catalyst for producing monocyclic aromatic hydrocarbons is preferably in a gaseous state. In addition, the feedstock may be optionally diluted with gas.

(Catalyst for Producing Monocyclic Aromatic Hydrocarbons)

The catalyst for producing monocyclic aromatic hydrocarbons contains a crystalline aluminosilicate.

[Crystalline Aluminosilicate]

The crystalline aluminosilicate is preferably a medium-pore zeolite and/or a large-pore zeolite since the yield of monocyclic aromatic hydrocarbons can be further increased.

The medium-pore zeolite is a zeolite having a skeletal structure of 10-membered rings, and examples thereof include zeolites having crystal structures of AEL type, EUO type, FER type, HEU type, MEL type, MFI type, NES type, TON type, and WEI type. Among these, the MFI type is preferable since this can further increase the yield of monocyclic aromatic hydrocarbons.

A large-pore zeolite is a zeolite having a skeletal structure of 12-membered rings, and examples thereof include zeolites having crystal structures of AFI type, ATO type, BEA type, CON type, FAU type, GME type, LTL type, MOR type, MTW type, and OFF type. Among these, the BEA type, FAU type, and MOR type are preferable since these can be industrially used. Moreover, the BEA type and MOR type are more preferable since these can further increase the yield of monocyclic aromatic hydrocarbons.

The crystalline aluminosilicate may contain, in addition to the medium-pore zeolite and the large-pore zeolite, a small-pore zeolite having a skeletal structure of 10 or less-membered rings or an ultralarge-pore zeolite having a skeletal structure of 14 or more-membered rings.

Examples of the small-pore zeolite include zeolites having crystal structures of ANA type, CHA type, ERI type, GIS type, KFI type, LTA type, NAT type, PAU type, and YUG type.

Examples of the ultralarge-pore zeolite include zeolites having crystal structures of CLO type and VPI type.

If the cracking and reforming reaction step is performed by a reaction in a fixed bed, provided that a total amount of the catalyst for producing monocyclic aromatic hydrocarbons is 100 mass %, the content of the crystalline aluminosilicate in the catalyst for producing monocyclic aromatic hydrocarbons is preferably 60 mass % to 100 mass %, more preferably 70 mass % to 100 mass %, and particularly preferably 90 mass % to 100 mass %. If the content of the crystalline aluminosilicate is 60 mass % or more, the yield of the monocyclic aromatic hydrocarbons can be sufficiently increased.

If the cracking and reforming reaction step is performed by a reaction in a fluidized bed, provided that a total amount of the catalyst for producing monocyclic aromatic hydrocarbons is 100 mass %, the content of the crystalline aluminosilicate in the catalyst for producing monocyclic aromatic hydrocarbons is preferably 20 mass % to 60 mass %, more preferably 30 mass % to 60 mass %, and particularly preferably 35 mass % to 60 mass %. If the content of the crystalline aluminosilicate is 20 mass % or more, the yield of the monocyclic aromatic hydrocarbons can be sufficiently increased. If the content of the crystalline aluminosilicate exceeds 60 mass %, the content of a binder that can be compounded with the catalyst decreases, whereby the catalyst becomes inappropriate for being used for the fluidized bed in some cases.

[Gallium and Zinc]

The catalyst for producing monocyclic aromatic hydrocarbons can optionally contain gallium and/or zinc. If the catalyst contains gallium and/or zinc, the proportion of the monocyclic aromatic hydrocarbons produced can be further increased.

Gallium may be contained in the catalyst for producing monocyclic aromatic hydrocarbons, for example, in a form in which the gallium is incorporated into a lattice skeleton of the crystalline aluminosilicate (crystalline aluminogallosilicate), in a form in which the gallium is supported on the crystalline aluminosilicate (gallium-supported crystalline aluminosilicate), or in a form as a combination of the above two forms.

Zinc may be contained in the catalyst for producing monocyclic aromatic hydrocarbons, for example, in a form in which the zinc is incorporated into a lattice skeleton of the crystalline aluminosilicate (crystalline aluminozincosilicate), in a form in which the zinc is supported on the crystalline aluminosilicate (zinc-supported crystalline aluminosilicate), or in a form as a combination of the above two forms.

The crystalline aluminogallosilicate and the crystalline aluminozincosilicate have a structure in which $SiO_4$, $AlO_4$ and $GaO_4/ZnO_4$ structures are present in the skeleton. Moreover, the crystalline aluminogallosilicate and the crystalline aluminozincosilicate are obtained by, for example, gel crystallization caused by hydrothermal synthesis, a method of inserting gallium or zinc into a lattice skeleton of the crystalline aluminosilicate, or a method of inserting aluminum into a lattice skeleton of a crystalline gallosilicate or a crystalline zincosilicate.

The gallium-supported crystalline aluminosilicate is obtained by causing gallium to be supported on the crystalline aluminosilicate by a known method such as an ion-exchange method or an impregnation method. A source of gallium used at this time is not particularly limited, and examples thereof include gallium salts such as gallium nitrate and gallium chloride, gallium oxide, and the like.

The zinc-supported crystalline aluminosilicate is obtained by causing zinc to be supported on the crystalline aluminosilicate by a known method such as an ion-exchange method or an impregnation method. A source of zinc used at this time is not particularly limited, and examples thereof include zinc salts such as zinc nitrate and zinc chloride, zinc oxide, and the like.

If the catalyst for producing monocyclic aromatic hydrocarbons contains gallium and/or zinc, provided that the total amount of the catalyst is 100 mass %, the content of gallium and/or zinc in the catalyst for producing monocyclic aromatic hydrocarbons is preferably 0.01 mass % to 5.0 mass %, and more preferably 0.05 mass % to 2.0 mass %. If the content of gallium and/or zinc is 0.01 mass % or more, a proportion of monocyclic aromatic hydrocarbons produced can be further increased, and if the content is 5.0 mass % or less, the yield of monocyclic aromatic hydrocarbons can be further increased.

[Phosphorus and Boron]

It is preferable that the catalyst for producing monocyclic aromatic hydrocarbons contains phosphorus and/or boron. If the catalyst for producing monocyclic aromatic hydrocarbons contains phosphorus and/or boron, it is possible to prevent the yield of monocyclic aromatic hydrocarbons from decreasing over time and to inhibit coke from being deposited on the catalyst surface.

Examples of methods of adding phosphorus to the catalyst for producing monocyclic aromatic hydrocarbons include a method of causing phosphorus to be supported on the crystalline aluminosilicate, the crystalline aluminogallosilicate, or the crystalline aluminozincosilicate by an ion-exchange method, an impregnation method, or the like, a method of adding a phosphorus compound to the catalyst during the synthesis of the zeolite and replacing a portion of the crystalline aluminosilicate inside the skeleton thereof with phosphorus, a method of using a crystallization accelerator containing phosphorus during the synthesis of a zeolite, and the like. The aqueous solution containing phosphate ions used at this time is not particularly limited, and aqueous solutions prepared by dissolving phosphoric acid, diammonium hydrogen phosphate, ammonium dihydrogen phosphate, and other water-soluble phosphoric acid salts in water at arbitrary concentrations can be preferably used.

Examples of methods of adding boron to the catalyst for producing monocyclic aromatic hydrocarbons include a method of causing boron to be supported on the crystalline aluminosilicate, the crystalline aluminogallosilicate, or the crystalline aluminozincosilicate by an ion-exchange method, an impregnation method, or the like, a method of adding a boron compound to the catalyst during the synthesis of the zeolite and replacing a portion of the crystalline aluminosilicate inside the skeleton thereof with boron, a method of using a crystallization accelerator containing boron during the synthesis of a zeolite, and the like.

Provided that a total amount of the catalyst is 100 mass %, the content of phosphorus and/or boron in the catalyst for producing monocyclic aromatic hydrocarbons is preferably 0.1 mass % to 10 mass %, more preferably 0.5 mass % to 9 mass %, and even more preferably 0.5 mass % to 8 mass %. If the content of phosphorus and/or boron is 0.1 mass % or more, decrease in the yield caused over time can be more reliably prevented, and if the content is 10 mass % or less, the yield of monocyclic aromatic hydrocarbons can be further increased.

[Shape]

The catalyst for producing monocyclic aromatic hydrocarbons has the shape of, for example, powder, granules, or pellets, depending on the reaction type. For example, the catalyst is formed into powder when used in a fluidized bed, and formed into granules or pellets when used in a fixed bed. The average particle size of the catalyst used in a fluidized bed is preferably 30 μm to 180 μm, and more preferably 50 μm to 100 μm. Moreover, the bulk density of the catalyst used in a fluidized bed is preferably 0.4 g/cc to 1.8 g/cc, and more preferably 0.5 g/cc to 1.0 g/cc.

The average particle size is a size of particles accounting for 50 mass % in a particle size distribution obtained by classification conducted by means of sieving, and the bulk density is a value measured by the method specified by JIS Standard R9301-2-3.

In order to obtain a granular or pellet-like catalyst, an inert oxide as a binder may be optionally compounded with the catalyst, and the resultant may be molded by various types of molding machines.

When the catalyst for producing monocyclic aromatic hydrocarbons contains an inorganic oxide such as a binder, a phosphorus-containing binder may be used.

(Reaction Temperature)

The reaction temperature at the time when the oil feedstock is brought into contact and reacts with the catalyst for producing monocyclic aromatic hydrocarbons is not particularly limited, but the temperature is preferably 400° C. to 650° C. If the lower limit of the reaction temperature is 400° C. or higher, this makes it easy to cause the oil feedstock to react. The lower limit is more preferably 450° C. or higher. Moreover, if the upper limit of the reaction temperature is 650° C. or lower, the yield of monocyclic aromatic hydrocarbons can be sufficiently increased. The upper limit is more preferably 600° C. or lower.

(Reaction Pressure)

The reaction pressure at the time when the oil feedstock is brought into contact and reacts with the catalyst for producing monocyclic aromatic hydrocarbons is preferably 1.5 MPaG or lower, and more preferably 1.0 MPaG or lower. If the reaction pressure is 1.5 MPaG or lower, production of light-gas as a by-product can be prevented, and the pressure resistance of the reaction apparatus can be lowered.

(Contact Time)

The time during which the oil feedstock comes into contact with the catalyst for producing monocyclic aromatic hydrocarbons is not particularly limited, as long as a desired reaction virtually proceeds. However, for example, the contact time is preferably 1 second to 300 seconds in terms of the time during which gas passes on the catalyst for producing monocyclic aromatic hydrocarbons. The lower limit of the contact time is more preferably 5 seconds, and the upper limit thereof is more preferably 150 seconds. If the contact time is 1 second or longer, the reaction can be reliably caused, and if the contact time is 300 seconds or shorter, it is possible to inhibit carbonaceous materials from accumulating on the catalyst due to excessive coking and the like, or to suppress the amount of light gas generated by cracking.

<Separation Step>

In the separation step, the product formed by the cracking and reforming reaction step is separated into plural fractions.

In order to separate the product into plural fractions, known distillation apparatuses or gas-liquid separation apparatuses may be used. An example of the distillation apparatus includes an apparatus that can distillate and separate plural fractions by means of a multistage distillation apparatus such as a stripper. An example of the gas-liquid separation apparatus includes an apparatus that includes a gas-liquid separation tank, a product inlet pipe for introducing the product into the gas-liquid separation tank, a gas component outflow pipe disposed in the upper portion of the gas-liquid separation tank, and a liquid component outflow pipe disposed in the lower portion of the gas-liquid separation tank.

In the separation step, at least a gas component and a liquid fraction are separated, and the liquid fraction is further separated into plural fractions. Examples of the separation step include an embodiment in which the product is separated into a gas component which mainly contains components having 4 or less carbon atoms (for example, hydrogen, methane, ethane, and LPG) and a liquid fraction, and an embodiment in which the product is separated into a gas component which contains components having 2 or less carbon atoms (for example, hydrogen, methane, and ethane) and a liquid fraction. The examples also include an embodiment in which the liquid fraction is further separated into a fraction containing monocyclic aromatic hydrocarbons and a heavy fraction, an embodiment in which the liquid fraction is further separated into LPG, a fraction containing monocyclic aromatic hydrocarbons, and a heavy fraction, an embodiment in which the liquid fraction is further separated into LPG, a fraction containing monocyclic aromatic hydrocarbons, and plural heavy fractions, and the like.

In the present embodiment, an embodiment is employed in which the product is separated into a gas component containing components having 4 or less carbon atoms (for example, hydrogen, methane, ethane, and LPG) and a liquid fraction, and the liquid fraction is further separated into a fraction containing monocyclic aromatic hydrocarbons having 6 to 8 carbon atoms and a fraction heavier than the above fraction (heavy fraction having 9 or more carbon atoms). Herein, in the heavy fraction having 9 or more carbon atoms that is separated by the separation step, the concentration of polycyclic aromatic hydrocarbons is extremely high, such as 50 mass % to 95 mass %, though the concentration varies with the properties of the oil feedstock or the conditions of the cracking and reforming reaction step, the separation step, and the like.

<Purification and Recovery Step>

In the purification and recovery step, the monocyclic aromatic hydrocarbons having 6 to 8 carbon atoms obtained by the separated step are purified and recovered.

Since the fraction heavier than the monocyclic aromatic hydrocarbons has been separated by the separation step, in this purification and recovery step, a step of separately recovering each of benzene, toluene, and xylene from the fraction containing monocyclic aromatic hydrocarbons having 6 to 8 carbon atoms is employed. The fraction heavier than the monocyclic aromatic hydrocarbons is a heavy fraction having 9 or more carbon atoms. This fraction contains polycyclic aromatic hydrocarbons as a main component and particularly contains a large amount of bicyclic aromatic hydrocarbons such as naphthalenes.

When an embodiment in which the liquid fraction is not fractionated is employed as the separation step, a step of separating and removing a fraction heavier than monocyclic aromatic hydrocarbons from the liquid fraction and separately recovering each of benzene, toluene, and xylene (monocyclic aromatic hydrocarbons having 6 to 8 carbon atoms) as monocyclic aromatic hydrocarbons is employed as the purification and recovery step.

Moreover, when the liquid fraction is not advantageously fractionated by the separation step, and the recovered monocyclic aromatic hydrocarbons having 6 to 8 carbon atoms contain a large amount of fractions other than the monocyclic aromatic hydrocarbons, it is particularly preferable to separate the heavy fraction having 9 or more carbon atoms from this fraction and to supply the heavy fraction to the second returning step which will be described later. The fraction heavier than the monocyclic aromatic hydrocarbons contains polycyclic aromatic hydrocarbons as a main component and particularly contains a large amount of bicyclic aromatic hydrocarbons such as naphthalenes.

<First Returning Step>

In the first returning step, at least a portion of toluene obtained by the purification and recovery step is returned to the cracking and reforming reaction step.

That is, in the first returning step, among benzene, toluene, and xylene, which are separately obtained by means of distillation and purification in the purification and recovery step, at least a portion of toluene is returned to the cracking and reforming reaction step. By being returned to the cracking and reforming reaction step, the toluene causes a reaction such as disproportionation in this step as described above and is converted into benzene and xylene.

That is, if a disproportionation reaction occurs, theoretically, 1 mol of benzene and 1 mol of xylene are produced from 2 mol of toluene. The produced benzene and xylene go through the separation step and the purification and recovery step, and as a result, they are recovered as benzene and xylene as products. In this manner, the yield of benzene and xylene can be increased.

The amount of toluene returned to the cracking and reforming reaction step is set within a range in which a reaction such as the disproportionation reaction of toluene as described above occurs advantageously in the cracking and reforming reaction step without negatively affecting the reaction for obtaining a product containing monocyclic aromatic hydrocarbons having 6 to 8 carbon atoms and a heavy fraction having 9 or more carbon atoms from oil feedstock as described above. Such an amount can be determined in advance by experiment or simulation.

<Second Returning Step>

In the second returning step, the heavy fraction having 9 or more carbon atoms separated from the product formed by the cracking and reforming reaction step is returned to the cracking and reforming reaction step. That is, the heavy fraction having 9 or more carbon atoms separated by the separation step is returned to the cracking and reforming reaction step. Moreover, as described above, when the liquid fraction is not advantageously fractionated by the separation step, and the recovered monocyclic aromatic hydrocarbons having 6 to 8 carbon atoms (benzene, toluene, and xylene) contain the heavy fraction having 9 or more carbon atoms in addition to the monocyclic aromatic hydrocarbons, this fraction is separated and returned to the cracking and reforming reaction step (supplied to the second returning step).

The second returning step may be performed independently of the first returning step. However, in order to simplify the constitution of the apparatus, it is preferable to constitute the apparatus such that a route such as a pipe constituting the second returning step is joined to a route such as a pipe constituting the first returning step as shown in FIG. 1.

If the heavy fraction having 9 or more carbon atoms is returned to the cracking and reforming reaction step in this way, by cracking the monocyclic aromatic hydrocarbons having 9 or more carbon atoms as described above, monocyclic aromatic hydrocarbons having 6 to 8 carbon atoms can be obtained. Moreover, if the monocyclic aromatic hydrocarbons having 9 or more carbon atoms coexist with toluene, a transalkylation reaction can more easily occur. As a result, the yield of monocyclic aromatic hydrocarbons having 6 to 8 carbon atoms, particularly, the yield of benzene and xylene can be increased.

<Hydrogen Recovery Step>

In the hydrogen recovery step, hydrogen is recovered from a gas component obtained by the separation/recovery step.

The method of recovering hydrogen is not particularly limited as long as hydrogen contained in the gas component obtained by the separation step and other gases can be separated. Examples of the method include a Pressure Swing Adsorption method (PSA method), a cryogenic separation method, a membrane separation method, and the like.

In the method for producing monocyclic aromatic hydrocarbons of the present embodiment, by the cracking and reforming reaction step, oil feedstock is brought into contact with a catalyst for producing monocyclic aromatic hydrocarbons containing a crystalline aluminosilicate to cause a reaction. Accordingly, monocyclic aromatic hydrocarbons having 6 to 8 carbon atoms can be produced at a high yield.

Moreover, since the method includes the first returning step of returning at least a portion of toluene obtained by the purification and recovery step to the cracking and reforming reaction step, by causing a reaction such as disproportionation of toluene in the cracking and reforming reaction step, benzene and xylene can be obtained from toluene. Accordingly, particularly when the demand for benzene or xylene is relatively higher than that for toluene, benzene or xylene can be produced in a larger amount such that the yield of benzene or xylene becomes higher than that of toluene.

In addition, since the method includes the second returning step of returning the heavy fraction having 9 or more carbon atoms separated from the product formed by the cracking and reforming reaction step to the cracking and reforming reaction step, by cracking the monocyclic aromatic hydrocarbons having 9 or more carbon atoms by the cracking and reforming reaction step, monocyclic aromatic hydrocarbons having 6 to 8 carbon atoms can be obtained. As a result, the yield of monocyclic aromatic hydrocarbons having 6 to 8 carbon atoms, particularly, the yield of benzene and xylene can be increased.

[Second Embodiment]

A second embodiment of the method for producing monocyclic aromatic hydrocarbons of the present invention will be described.

Figure 2:
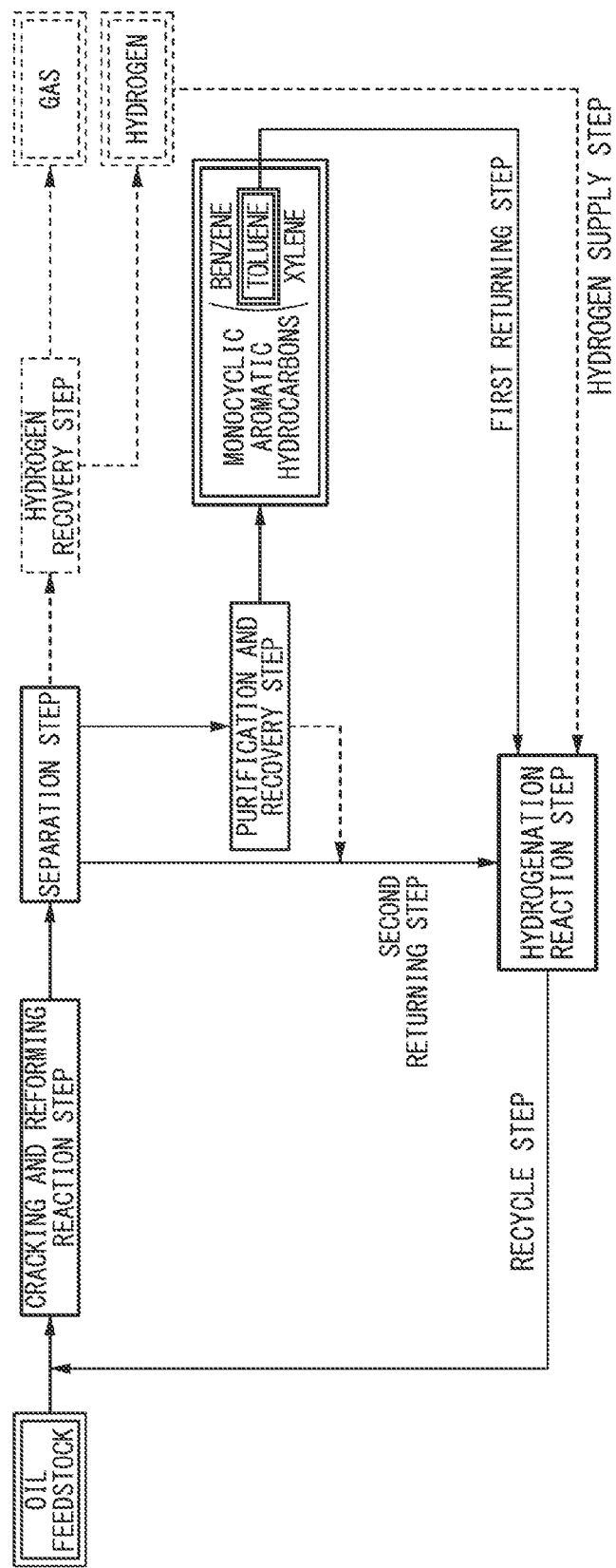
FIG. 2 is a view for illustrating a second embodiment of the method for producing monocyclic aromatic hydrocarbons of the present invention.

FIG. 2 is a view for illustrating the second embodiment of the method for producing monocyclic aromatic hydrocarbons of the present invention. The method for producing monocyclic aromatic hydrocarbons of the present embodiment is also a method for producing monocyclic aromatic hydrocarbons having 6 to 8 carbon atoms from oil feedstock.

That is, the method for producing monocyclic aromatic hydrocarbons of the present embodiment may include the respective steps shown in FIG. 2.

(7) A cracking and reforming reaction step of bringing oil feedstock into contact with a catalyst for producing monocyclic aromatic hydrocarbons to cause a reaction and obtain a product containing monocyclic aromatic hydrocarbons having 6 to 8 carbon atoms and a heavy fraction having 9 or more carbon atoms (8) A separation step of separating the product formed by the cracking and reforming reaction step into plural fractions (9) A purification and recovery step of purifying and recovering monocyclic aromatic hydrocarbons separated by the separation step

(10) A first returning step of returning at least a portion of toluene obtained by the purification and recovery step to the cracking and reforming reaction step

(11) A second returning step of returning the heavy fraction having 9 or more carbon atoms separated from the product formed by the cracking and reforming reaction step to the cracking and reforming reaction step

(12) A hydrogenation reaction step of hydrogenating the heavy fraction having 9 or more carbon atoms separated from the product formed by the cracking and reforming reaction step

(13) A recycle step of returning hydrogenation products obtained by the hydrogenation reaction step to the cracking and reforming reaction step

(14) A hydrogen recovery step of recovering hydrogen which is produced as a by-product by the cracking and reforming reaction step, from a gas component separated by the separation step

(15) A hydrogen supply step of supplying the hydrogen recovered by the hydrogen recovery step to the hydrogenation reaction step Among the steps (7) to (15), the steps (7), (9), (10), (12), and (13) are steps included in the third embodiment of the present invention, and the steps (8), (11), (14), and (15) are optional steps.

The (7) cracking and reforming reaction step can be performed in the same manner as the (1) cracking and reforming reaction step in the first embodiment.

The (8) separation step can be performed in the same manner as the (2) separation step in the first embodiment.

The (9) purification and recovery step can be performed in the same manner as the (3) purification and recovery step in the first embodiment.

In the (10) first returning step, at least a portion of toluene obtained by the (9) purification and recovery step is supplied into a middle portion of a hydrogenation reactor used in the (12) hydrogenation reaction step which will be described later, whereby the toluene is indirectly returned to the (7) cracking and reforming reaction step.

In the (11) second returning step, the heavy fraction having 9 or more carbon atoms separated from the product formed by the (7) cracking and reforming reaction step is supplied to the (12) hydrogenation reaction step which will be described later, whereby the heavy fraction having 9 or more carbon atoms is indirectly returned to the (7) cracking and reforming reaction step.

The (14) hydrogen recovery step can be performed in the same manner as the (6) hydrogen recovery step in the first embodiment.

<Hydrogenation Reaction Step>

In the (12) hydrogenation reaction step, the heavy fraction having 9 or more carbon atoms separated from the product of the cracking and reforming reaction step is hydrogenated. Specifically, the heavy fraction and hydrogen are supplied to a hydrogenation reactor, and by using a hydrogenation catalyst, at least a portion of polycyclic aromatic hydrocarbons contained in the mixture is subjected to hydrogenation treatment. Herein, the (11) second returning step includes a step of supplying the heavy fraction having 9 or more carbon atoms separated from the product formed by the cracking and reforming reaction step to the hydrogenation reaction step. That is, the second returning step includes the hydrogenation reaction step and the recycle step following the hydrogenation reaction step so as to function as a step of returning the heavy fraction having 9 or more carbon atoms separated from the product formed by the cracking and reforming reaction step to the cracking and reforming reaction step. Here, the (11) second returning step may be performed independently of the hydrogenation reaction step and the recycle step, such that the heavy fraction directly returns to the cracking and reforming reaction step without passing through the hydrogenation reaction step and the recycle step. In this case, the second returning step is substantially performed in two ways.

The heavy fraction having 9 or more carbon atoms separated by the separation step and the purification and recovery step is supplied to the hydrogenation reaction step. The heavy fraction supplied to the hydrogenation reaction step, that is, the heavy fraction having 9 or more carbon atoms contains a large amount of bicyclic aromatic hydrocarbons (polycyclic aromatic hydrocarbons) such as naphthalene.

Therefore, in the hydrogenation reaction step, it is preferable that the polycyclic aromatic hydrocarbons be hydrogenated until one aromatic ring remains. For example, it is preferable for naphthalene to be hydrogenated until it becomes tetralin (naphthenobenzene). Alkylnaphthalene such as methylnaphthalene or dimethylnaphthalene also preferably becomes naphthenobenzene, that is, an aromatic hydrocarbon with one aromatic ring having a tetralin skeleton. Likewise, indenes preferably become aromatic hydrocarbons having an indane skeleton, anthracenes preferably become aromatic hydrocarbons having an octahydroanthracene skeleton, and phenanthrenes preferably become aromatic hydrocarbons having an octahydrophenanthrene skeleton.

If hydrogenation is performed until only one aromatic ring remains, when the hydrogenation products are returned to the cracking and reforming step by the recycle step which will be described later, the hydrogenation products, particularly, aromatic hydrocarbons having a tetralin skeleton are easily converted into monocyclic aromatic hydrocarbons. In order to increase the yield of monocyclic aromatic hydrocarbons in the cracking and reforming step in this manner, the content of polycyclic aromatic hydrocarbons in the hydrogenation products obtained by the hydrogenation reaction step is preferably set to 40 mass % or less, more preferably set to 25 mass % or less, and even more preferably set to 15 mass % or less.

Moreover, the content of polycyclic aromatic hydrocarbons in the obtained hydrogenation products is preferably smaller than the content of polycyclic aromatic hydrocarbons of the oil feedstock. The content of polycyclic aromatic hydrocarbons in the hydrogenation products, that is, the concentration of polycyclic aromatic hydrocarbons can be decreased by means of increasing the amount of the hydrogenation catalyst or increasing the reaction pressure. Here, it is not necessary to perform the hydrogenation treatment until all of the polycyclic aromatic hydrocarbons become saturated hydrocarbons. If hydrogenation is performed excessively, the amount of consumed hydrogen increases, and the amount of heat generated increases excessively.

As the reaction type in the hydrogenation reaction step, a fixed bed is preferably employed.

As the hydrogenation catalyst, known hydrogenation catalysts (for example, nickel catalysts, palladium catalysts, nickel-molybdenum-based catalysts, cobalt-molybdenum-based catalysts, nickel-cobalt-molybdenum-based catalysts, and nickel-tungsten-based catalysts) can be used.

The hydrogenation reaction temperature varies with the type of the hydrogenation reaction catalyst used, but it is generally in a range of 100° C. to 450° C., more preferably in a range of 200° C. to 400° C., and even more preferably in a range of 250° C. to 380° C.

The hydrogenation reaction pressure is preferably from 0.7 M Pa to 13 MPa. Particularly, it is preferably from 1 MPa to 10 MPa, and more preferably from 1 MPa to 7 MPa. If the hydrogenation reaction pressure is 13 MPa or lower, a hydrogenation reactor having a relatively low durable pressure can be used, and the cost of the equipment can be reduced. Moreover, since the pressure of hydrogen recovered by the hydrogen recovery step is generally 13 MPa or lower, the recovered hydrogen can be used without increasing pressure. On the other hand, if the pressure is 0.7 MPa or higher, the yield of the hydrogenation reaction can be maintained sufficiently at an appropriate level.

The amount of hydrogen consumed is preferably 3,000 scfb (506 $Nm^3/m^3$) or less, more preferably 2,500 scfb (422 $Nm^3/m^3$) or less, and even more preferably 1,500 scfb (253 $Nm^3/m^3$) or less.

On the other hand, in view of the yield of the hydrogenation reaction, the amount of hydrogen consumed is preferably 300 scfb (50 $Nm^3/m^3$) or more.

The Liquid Hourly Space Velocity (LHSV) of the heavy fraction is preferably from 0.1 $h^{-1}$ to 20 $h^{-1}$, and more preferably from 0.2 $h^{-1}$ to 10 $h^{-1}$. If the LHSV is 20 $h^{-1}$ or less, polycyclic aromatic hydrocarbons can be sufficiently hydrogenated at a lower hydrogenation reaction pressure. On the other hand, if it is 0.1 $h^{-1}$ or more, increase in the scale of the hydrogenation reactor can be avoided.

Herein, the polycyclic aromatic hydrocarbons, for example, bicyclic aromatic hydrocarbons accounting for most of the polycyclic aromatic hydrocarbon generate an extremely large amount of heat during the hydrogenation reaction. Accordingly, in the case of a feedstock containing the polycyclic aromatic hydrocarbon in a large proportion, it is desirable to use a technique of suppressing excessive increase in the reaction temperature for stably performing the reaction. In the present embodiment, it is possible to employ a general method as the reaction temperature suppression method, and a technique such as circulating hydrogen gas quenching that is employed for desulfurization apparatuses for kerosene and diesel oil can be employed. However, in the heavy fraction separated by the separation step, the concentration of polycyclic aromatic hydrocarbons is extremely high, for example, 50 mass % to 95 mass %. Therefore, if it is desired to suppress heat generation by only hydrogen quenching, the number of required quenching equipment becomes close to being double digits, and the peripheral constitution of the reaction apparatus for suppressing heat generation becomes extremely complicated. Moreover, since the reaction apparatus becomes an apparatus generating an extremely large amount of heat, it may be evaluated to be an apparatus having a high risk in an emergency of the operation.

Accordingly, in the present embodiment, as described above, the toluene returned to the cracking and reforming reaction step by the first returning step is supplied to a middle portion (a portion between an inlet and an outlet of the hydrogenation reactor) of the hydrogenation reactor used in the hydrogenation reaction step. If the toluene is supplied to the middle portion of the hydrogenation reactor in this manner, the toluene is not hydrogenated and vaporizes simply by being exposed to a high temperature inside the hydrogenation reactor. Consequently, the toluene functions as a coolant (quenching agent) by depriving the vaporization heat of the inside of the hydrogenation reactor. That is, if the toluene is supplied to the middle portion of the hydrogenation reactor, heat generated by the hydrogenation of the polycyclic aromatic hydrocarbons is reduced in the hydrogenation reaction step, whereby the hydrogenation reaction can be sufficiently performed to an appropriate degree even in a generally used conventional hydrogenation reactor. This is a method according to the fourth embodiment of the present invention.

Furthermore, in addition to the toluene, if a fraction containing monocyclic aromatic hydrocarbons having 9 or more carbon atoms is separated by the purification and recovery step, or if a fraction containing monocyclic aromatic hydrocarbon having 9 to 10 or more carbon atoms is selectively separated by the separation step, these fractions can also be used as a coolant together with toluene. Moreover, in addition to the toluene, hydrocarbons other than toluene may be concurrently used as a diluent.

<Recycle Step>

In the (13) recycle step, the hydrogenation products of the mixture obtained by the hydrogenation reaction step are returned to the cracking and reforming reaction step by being mixed with oil feedstock or separately returned to the cracking and reforming reaction step.

By returning the hydrogenation products of the mixture to the cracking and reforming reaction step, the heavy fraction as a by-product can also be used as a feedstock to obtain monocyclic aromatic hydrocarbons. Therefore, it is possible to reduce the amount of the by-product and to increase the amount of monocyclic aromatic hydrocarbons produced. Moreover, since saturated hydrocarbons are also produced by hydrogenation, the hydrogen transfer reaction in the cracking and reforming reaction step can be accelerated. For these reasons, the overall yield of monocyclic aromatic hydrocarbons based on the amount of the oil feedstock supplied can be increased.

Herein, regarding the hydrogenation products of the heavy fraction obtained by the hydrogenation reaction step, after a gas component is separated and removed first, the resultant may go through the recycle step and returns to the cracking and reforming reaction step, or a portion thereof can be supplied as a diluent to the hydrogenation reaction step.

In the recycle step, the entire hydrogenation products are not necessarily recycled for the oil feedstock of the cracking and reforming reaction step. In this case, the hydrogenation products that are not recycled can be used as a base material of fuel.

Furthermore, when the heavy fraction is returned as is to the cracking and reforming reaction step without being subjected to hydrogenation treatment, since the reactivity of polycyclic aromatic hydrocarbons is low, the yield of the monocyclic aromatic hydrocarbons hardly increases.

<Hydrogen Supply Step>

In the hydrogen supply step, the hydrogen obtained by the hydrogen recovery step is supplied into the hydrogenation reactor of the hydrogenation reaction step. The amount of the hydrogen supplied at this time is adjusted according to the amount of the mixture supplied to the hydrogenation reaction step. In addition, if necessary, the pressure of the hydrogen is regulated.

Since the present embodiment includes the hydrogen supply step, the mixture can be hydrogenated by using the hydrogen which is produced as a by-product by the cracking and reforming reaction step. If a portion of the hydrogen or the entire hydrogen is prepared from the hydrogen as a by-product, the amount of a portion of the hydrogen or the entire hydrogen supplied from the outside can be reduced.

Since the method for producing monocyclic aromatic hydrocarbons of the present embodiment includes the hydrogenation reaction step and the recycle step, the heavy fraction as a by-product can also be used as a feedstock to obtain monocyclic aromatic hydrocarbons. Accordingly, it is possible to reduce the amount of the by-product and to increase the amount of monocyclic aromatic hydrocarbons produced. Accordingly, monocyclic aromatic hydrocarbons having 6 to 8 carbon atoms can be produced at a high yield from oil feedstock containing polycyclic aromatic hydrocarbons.

Furthermore, since at least a portion of the toluene obtained by the purification and recovery step is supplied into the middle portion of the hydrogenation reactor used in the hydrogenation reaction step, the toluene can function as a coolant (quenching agent). Consequently, it is possible to reduce heat generated by the hydrogenation of polycyclic aromatic hydrocarbons in the hydrogenation reaction step, whereby the hydrogenation reaction can be sufficiently performed to an appropriate degree even in a generally used conventional hydrogenation reactor.

Moreover, the toluene returns to the cracking and reforming reaction step through the recycle step without being hydrogenated by the hydrogenation reaction step. Accordingly, by causing a reaction such as disproportionation of toluene in the cracking and reforming reaction step, a large amount of benzene or xylene can be produced at a yield higher than that of toluene, as in the first embodiment.

[Third Embodiment]

A third embodiment of the method for producing monocyclic aromatic hydrocarbons of the present invention will be described.

Figure 3:
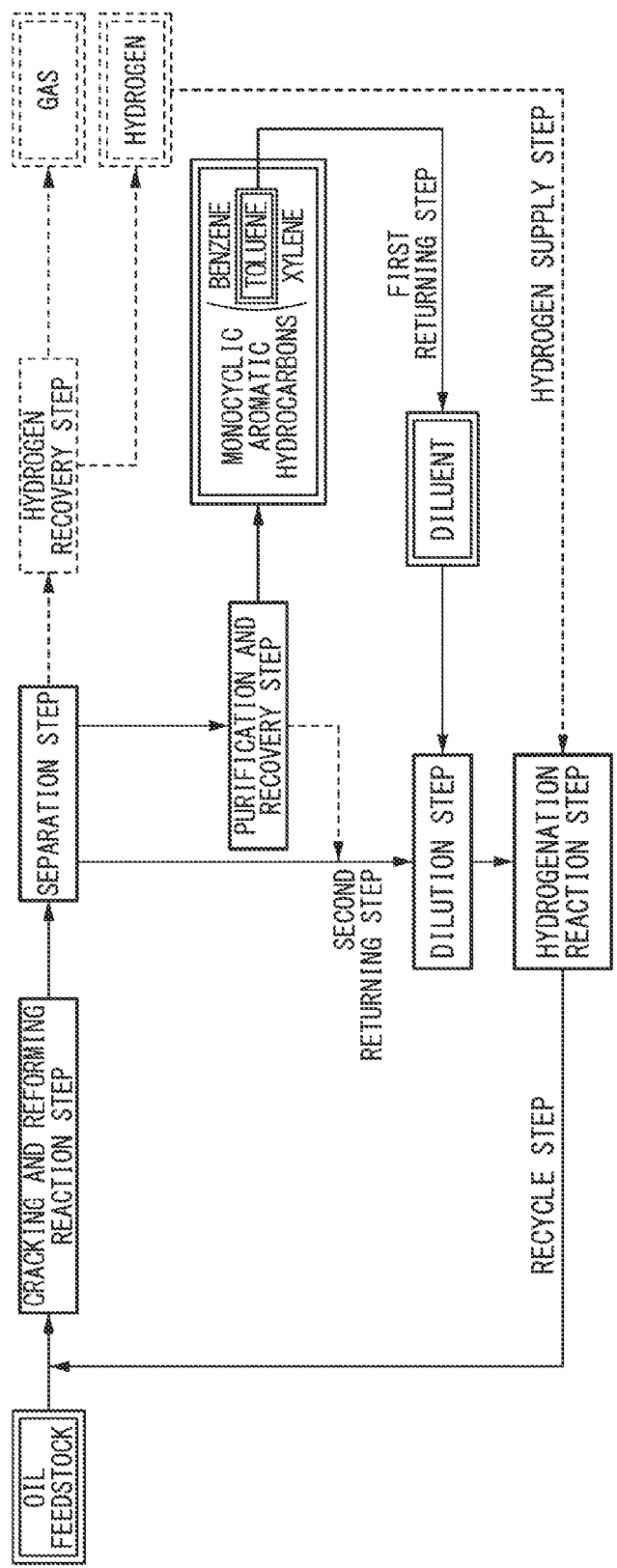
FIG. 3 is a view for illustrating a third embodiment of the method for producing monocyclic aromatic hydrocarbons of the present invention.

FIG. 3 is a view for illustrating the third embodiment of the method for producing monocyclic aromatic hydrocarbons of the present invention. The method for producing monocyclic aromatic hydrocarbons of the present embodiment is also a method for producing monocyclic aromatic hydrocarbons having 6 to 8 carbon atoms from oil feedstock.

That is, the method for producing monocyclic aromatic hydrocarbons of the present embodiment may include the respective steps shown in FIG. 3.

(16) A cracking and reforming reaction step of bringing oil feedstock into contact with a catalyst for producing monocyclic aromatic hydrocarbons to cause a reaction and obtain a product containing monocyclic aromatic hydrocarbons having 6 to 8 carbon atoms and a heavy fraction having 9 or more carbon atoms

(17) A separation step of separating the product formed by the cracking and reforming reaction step into plural fractions

(18) A purification and recovery step of purifying and recovering monocyclic aromatic hydrocarbons separated by the separation step

(19) A first returning step of returning at least a portion of toluene obtained by the purification and recovery step to the cracking and reforming reaction step

(20) A second returning step of returning the heavy fraction having 9 or more carbon atoms separated from the product formed by the cracking and reforming reaction step to the cracking and reforming reaction step

(21) A dilution step of adding a diluent to the heavy fraction having 9 or more carbon atoms separated from the product formed by the cracking and reforming reaction step

(22) A hydrogenation reaction step of hydrogenating a mixture obtained by the dilution step

(23) A recycle step of returning hydrogenation products of the mixture obtained by the hydrogenation reaction step to the cracking and reforming reaction step

(24) A hydrogen recovery step of recovering hydrogen produced as a by-product by the cracking and reforming reaction step, from a gas component separated by the separation step

(25) A hydrogen supply step of supplying the hydrogen recovered by the hydrogen recovery step to the hydrogenation reaction step Among the steps (16) to (25), the steps (16), (18), (19), (21), (22), and (23) are steps included in the fifth and sixth embodiments, and the steps (17), (20), (24), and (25) are optional steps.

The (16) cracking and reforming reaction step can be performed in the same manner as the (1) cracking and reforming reaction step in the first embodiment.

The (17) separation step can be performed in the same manner as the (2) separation step in the first embodiment.

The (18) purification and recovery step can be performed in the same manner as the (3) purification and recovery step in the first embodiment.

In the (19) first returning step, at least a portion of toluene is supplied to the (21) dilution step which will be describe later, whereby the toluene is indirectly returned to the (16) cracking and reforming reaction step.

In the (20) second returning step, the heavy fraction having 9 or more carbon atoms separated from the product formed by the (16) cracking and reforming reaction step is supplied to the (22) hydrogenation reaction step through the (21) dilution step which will be described later, whereby the heavy fraction having 9 or more carbon atoms is indirectly returned to the (16) cracking and reforming reaction step.

The (22) hydrogenation reaction step can be performed in the same manner as the (12) hydrogenation reaction step in the second embodiment.

The (23) recycle step can be performed in the same manner as the (13) recycle step in the second embodiment.

The (24) hydrogen recovery step can be performed in the same manner as the (6) hydrogen recovery step in the first embodiment.

The (25) hydrogen supply step can be performed in the same manner as the (15) hydrogen supply step in the second embodiment.

<Dilution Step>

In the (21) dilution step, a diluent formed of a hydrocarbon is added to the heavy fraction having 9 or more carbon atoms separated from the product formed by the cracking and reforming reaction step, such that the concentration of polycyclic aromatic hydrocarbons in a mixture of the heavy fraction having 9 or more carbon atoms and the diluent becomes lower than the concentration of polycyclic aromatic hydrocarbons in the heavy fraction. As a result, the concentration of polycyclic aromatic hydrocarbons in the heavy fraction supplied to the hydrogenation reaction step which will be described later is reduced to an appropriate level.

In the present embodiment, as a diluent, at least a portion of the toluene obtained by the purification and recovery step, that is, the toluene returned to the cracking and reforming reaction step by the first returning step is used. Accordingly, the first returning step of the present embodiment includes the dilution step, the hydrogenation reaction step, and the recycle step. As it is not shown in FIG. 3, the rest of the toluene obtained by the purification and recovery step may be supplied to the middle portion (the portion between an inlet and an outlet of the hydrogenation reactor) of the hydrogenation reactor (hydrogenation reaction step) as in the second embodiment, such that the toluene functions as a coolant (quenching agent).

In the heavy fraction (heavy fraction which remains after the diluent is removed from the mixture) which is separated by the separation step and directly supplied to the hydrogenation reaction step, the concentration of polycyclic aromatic hydrocarbons is extremely high, for example, 50 mass % to 95 mass %. These polycyclic aromatic hydrocarbons, for example, bicyclic aromatic hydrocarbons accounting for most of the polycyclic aromatic hydrocarbons generate an extremely large amount of heat during the hydrogenation reaction.

In the present embodiment, toluene is used as a diluent, and by the dilution step, the concentration of polycyclic aromatic hydrocarbons in the oil (mixture) to be supplied to the hydrogenation reaction step is adjusted in advance. By doing this, it is possible to suppress heat generated by hydrogenation of the polycyclic aromatic hydrocarbons, whereby the hydrogenation reaction can be sufficiently performed to an appropriate degree even in a generally used conventional hydrogenation reactor.

In addition to the toluene, other hydrocarbons (other than toluene) can also be concurrently used as the diluent. When the present embodiment includes the first returning step of directly returning at least a portion of toluene obtained by the purification and recovery step to the cracking and reforming reaction step as in the first embodiment, or includes the first returning step of indirectly returning the toluene to the cracking and reforming reaction step by supplying the toluene to the hydrogenation reaction step as in the second embodiment, a hydrocarbon other than the toluene can be used alone as a diluent in the dilution step.

As the hydrocarbon diluent other than toluene, hydrocarbons that are not easily hydrogenated compared to polycyclic aromatic hydrocarbons in the hydrogenation reaction step, for example, monocyclic aromatic hydrocarbons such as trimethylbenzene and tetramethylbenzene (including various isomers thereof), cyclohexanes, naphthenes such as decalins, and hydrocarbons including paraffin and the like are preferably used. Under such circumstances, it is necessary to select a material compatible with the heavy fraction, and when the concentration of the polycyclic aromatic hydrocarbons is extremely high, it is desirable to select a monocyclic aromatic hydrocarbon or the like.

On the other hand, when the hydrogenation reaction conditions are set to a high pressure of, for example, 7 MPa or higher, the monocyclic aromatic hydrocarbon itself as a diluent may be hydrogenated in some cases. Therefore, it is necessary to select an appropriate solvent in accordance with the actual hydrogenation reaction conditions. When a monocyclic aromatic hydrocarbon is recovered and reused as a diluent, there is no problem because the monocyclic aromatic hydrocarbon also becomes a saturated hydrocarbon and can be used as a diluent, and the diluent can be used as is in the cracking and reforming reaction step without any problem. However, in this case, attention is required since there is a possibility that a sufficient heating reduction effect may not be obtained in the hydrogenation reaction step.

Regarding the diluent, if the concentration (content) of polycyclic aromatic hydrocarbons is lower than that of the heavy fraction, a diluent contains those polycyclic aromatic hydrocarbons may be used. However, under such circumstances, the heating reduction effect is diminished compared to a diluent not containing polycyclic aromatic hydrocarbons. Specifically, base materials for oil refinery that contain the monocyclic aromatic hydrocarbons, naphthenes, paraffins and the like as well as polycyclic aromatic hydrocarbons, for example, various cracking base materials and straight-run base materials, such as LCO that is also used as the oil feedstock, can also be used.

The concentration of polycyclic aromatic hydrocarbons in such a diluent may be any concentration that can reduce the concentration of polycyclic aromatic hydrocarbons in the mixture to be formed to an appropriate level. The concentration is preferably 50 mass % or less, more preferably 30 mass % or less, and even more preferably 20 mass % or less.

Such a diluent is stored in, for example, a storage tank prepared separately, and is supplied to a line for transporting the heavy fraction from the storage tank and mixed with the heavy fraction. In this manner, the concentration of polycyclic aromatic hydrocarbons in the obtained mixture is reduced to an appropriate level.

In the dilution step that use toluene or the hydrocarbon other than toluene, it is preferable to form the mixture by adding the diluent to the heavy fraction, such that the concentration of polycyclic aromatic hydrocarbons in the mixture of the heavy fraction having 9 or more carbon atoms separated from the product formed by the cracking and reforming reaction step and the diluent, that is, the mixture to be actually supplied to the hydrogenation reaction step, becomes 5 mass % to 50 mass %. It is more preferable to add the diluent such that the concentration of polycyclic aromatic hydrocarbons in the mixture becomes 15 mass % to 35 mass %.

If the concentration of polycyclic aromatic hydrocarbons in the mixture is 50 mass % or less, heat generated by the hydrogenation reaction in the hydrogenation reaction step which will be described later can be reduced. Therefore, it is possible to prevent an extreme increase in the reaction temperature in the hydrogenation reactor and to cause the hydrogenation reaction (for example, conversion of bicyclic aromatic hydrocarbons into nathenobenzenes) to an appropriate degree. Moreover, a general hydrogenation reactor can be used. If the concentration of polycyclic aromatic hydrocarbons in the mixture is 5 mass % or higher, the conversion of polycyclic aromatic hydrocarbons into nathenobenzenes, which is the main purpose of the hydrogenation reaction step, can be performed with a desired efficiency.

Here, if the concentration of polycyclic aromatic hydrocarbons in the mixture is too low, the efficiency of the conversion of polycyclic aromatic hydrocarbons into nathenobenzenes does not bring a sufficient profit in terms of cost, and accordingly, for example, the scale of the hydrogenation reactor needs to be increased. Therefore, in order to further increase the conversion efficiency, it is preferable to adjust the concentration of polycyclic aromatic hydrocarbons in the mixture to be 15 mass % or higher as described above. In order to sufficiently reduce heat generated by the hydrogenation reaction, it is more preferable to adjust the concentration of polycyclic aromatic hydrocarbons in the mixture to be 35 mass % or less.

In the dilution step, in order to adjust the concentration of polycyclic aromatic hydrocarbons in the mixture to the concentration described above, the amount of the diluent to be supplied is appropriately determined. At this time, the amount of the diluent is greatly influenced by the concentration of polycyclic aromatic hydrocarbons in the heavy fraction having 9 or more carbon atoms separated from the product formed by the cracking and reforming reaction step. That is, if the concentration of polycyclic aromatic hydrocarbons in the heavy fraction is high, the amount of the diluent needs to be relatively increased, and if the concentration of polycyclic aromatic hydrocarbons in the heavy fraction is low, the amount of the diluent can be relatively reduced. Moreover, when a hydrocarbon other than toluene is used as the diluent, the amount of the diluent is also greatly influenced by the concentration of polycyclic aromatic hydrocarbon in the diluent. That is, if the concentration of polycyclic aromatic hydrocarbons in the diluent is high, the amount of the diluent needs to be relatively increased, and if the concentration of polycyclic aromatic hydrocarbons in the diluent is low, the amount of the diluent can be relatively reduced.

Generally, the concentration of polycyclic aromatic hydrocarbons in the heavy fraction separated from the product by the separation step as described above is 50 mass % to 95 mass %.

Accordingly, particularly when a hydrocarbon other than toluene is used as a diluent to dilute the heavy fraction, the concentration of polycyclic aromatic hydrocarbons in the heavy fraction (product) and the concentration of polycyclic aromatic hydrocarbons in the diluent is measured based on, for example, JPI-5S-49 "Petroleum products—Hydrocarbon type test methods—High performance liquid chromatographic method" or confirmed by FID gas chromatography or 2-dimensional gas chromatography. In this manner, the mixing ratio between the heavy fraction and the diluent is determined such that the concentration of polycyclic aromatic hydrocarbons in the mixture having been diluted with the diluent becomes 5 mass % to 50 mass % and preferably becomes 15 mass % to 35 mass % as described above. Usually, when the concentration of polycyclic aromatic hydrocarbons of the diluent is, for example, 20 mass % or less, the mass ratio (mixing ratio) between the heavy fraction (heavy fraction having 9 or more carbon atoms that is separated from the product formed by the cracking and reforming reaction step and to be supplied to the hydrogenation reaction step) separated by the separation step and the diluent (heavy fraction:diluent) is adjusted to be within a range of 10:90 to 80:20. Furthermore, when toluene is used as the diluent, the concentration of polycyclic aromatic hydrocarbons can be calculated to be 0 mass %.

When the flow rate per unit time of the heavy fraction, which is supplied to the hydrogenation reaction step from the separation step, is constant, the diluent is added to the heavy fraction under the conditions in which the mass ratio falls within the above range, at a constant flow rate per unit time. When the flow rate per unit time of the heavy fraction changes, the flow rate of the diluent also changes in response to the change.

<Hydrogenation Reaction Step>

The hydrogenation reaction step can be performed in the same manner as the (12) hydrogenation reaction step in the second embodiment as described above. That is, the mixture formed by adding a diluent to the heavy fraction having 9 or more carbon atoms in the dilution step is hydrogenated in the same manner as the (12) hydrogenation reaction step in the second embodiment. Even in this hydrogenation reaction step, a portion of the toluene obtained by the purification and recovery step in the same manner as in the second embodiment may be supplied as a coolant (quenching agent) to a middle portion (a portion between an inlet and outlet of the hydrogenation reactor) of the hydrogenation reactor (hydrogenation reaction step). The toluene supplied as a diluent is not hydrogenated by this hydrogenation reaction. Accordingly, the toluene functions merely as a diluent that reduces the concentration of polycyclic aromatic hydrocarbons and reduces heat generated by the hydrogenation reaction.

<Recycle Step>

The recycle step can be performed in the same manner as the (13) recycle step in the second embodiment as described above. That is, the hydrogenation products of the mixture obtained by the hydrogenation reaction step are returned to the cracking and reforming reaction step by being mixed with oil feedstock or separately returned to the cracking and reforming reaction step.

If the hydrogenation products of the mixture are returned to the cracking and reforming reaction step by being mixed with oil feedstock or separately returned to the cracking and reforming reaction step, the toluene used as a diluent causes a reaction such as disproportionation, whereby benzene and xylene are produced. When a hydrocarbon other than toluene is used as a diluent, the hydrocarbon other than toluene, for example, naphthenes or paraffins contribute to the generation of monocyclic aromatic hydrocarbons in the cracking and reforming reaction step. Therefore, this diluent contributes to the increase in the yield of monocyclic aromatic hydrocarbons.

Since the method for producing monocyclic aromatic hydrocarbons of the present embodiment also includes the hydrogenation reaction step and the recycle step, the heavy fraction as a by-product can be used as a feedstock 1 to obtain monocyclic aromatic hydrocarbons. Accordingly, it is possible to reduce the amount of the by-product and to increase the amount of monocyclic aromatic hydrocarbons produced. As a result, monocyclic aromatic hydrocarbons having 6 to 8 carbon atoms can be produced at a high yield from oil feedstock containing polycyclic aromatic hydrocarbons.

Moreover, the method includes the dilution step of adding a diluent to the heavy fraction having 9 or more carbon atoms separated from the product formed by the cracking and reforming reaction step such that the concentration of polycyclic aromatic hydrocarbons in the obtained mixture becomes lower than the concentration of polycyclic aromatic hydrocarbons in the heavy fraction. Therefore, it is possible to stabilize the hydrogenation reaction by suppressing polycyclic aromatic hydrocarbons from generating heat to an extreme degree by hydrogenation in the hydrogenation reaction step, and to avoid the extensive increase in the cost of equipment of the hydrogenation reactor, whereby the hydrogenation reaction can be sufficiently performed to an appropriate degree even in a generally used conventional hydrogenation reactor.

In addition, in the present embodiment, at least a portion of the toluene obtained by the purification and recovery step is added as a diluent to the heavy fraction having 9 or more carbon atoms. Since toluene is not easily hydrogenated in the hydrogenation reaction step, the heat generated by the hydrogenation of polycyclic aromatic hydrocarbons can be more effectively suppressed.

Furthermore, the toluene is virtually not hydrogenated by the hydrogenation reaction step and returned to the cracking and reforming reaction step through the recycle step. That is, by causing a reaction such as disproportionation of toluene in the cracking and reforming reaction step, a larger amount of benzene or xylene can be produced at a yield higher than that of toluene as in the first embodiment.

[Fourth Embodiment]

A fourth embodiment of the method for producing monocyclic aromatic hydrocarbons of the present invention will be described.

Figure 4:
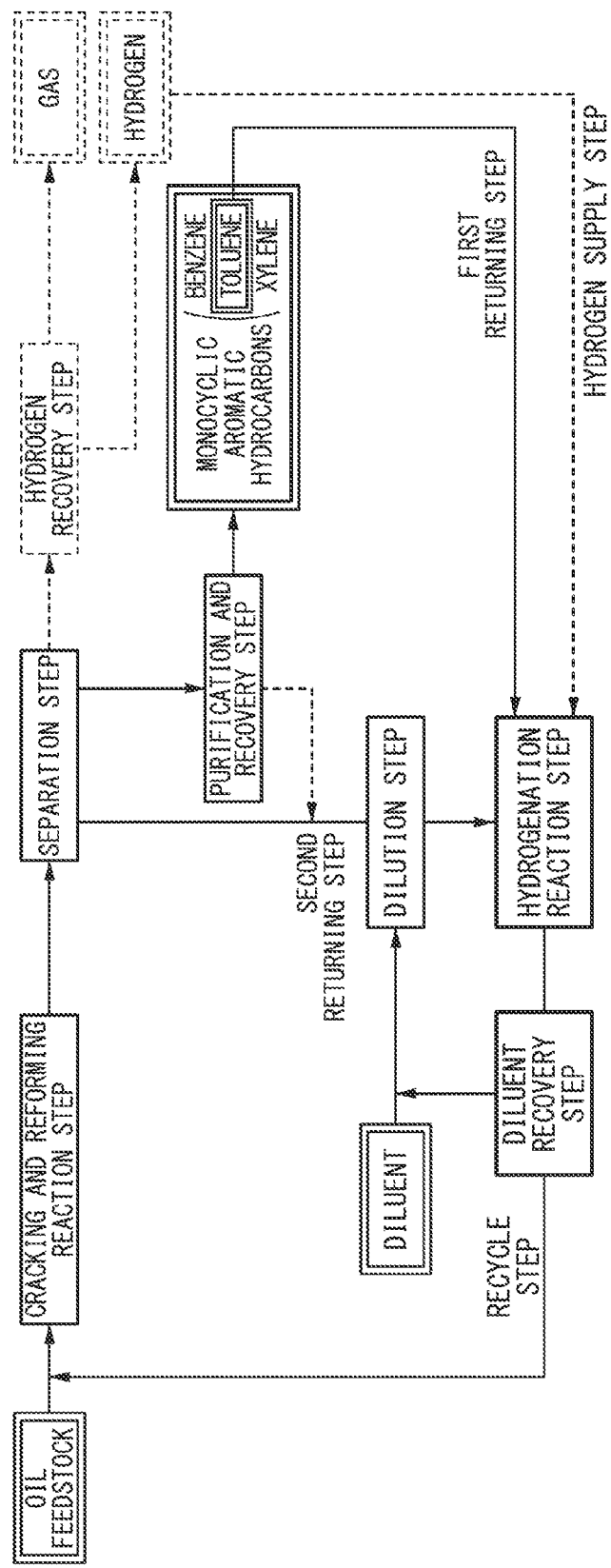
FIG. 4 is a view for illustrating a fourth embodiment of the method for producing monocyclic aromatic hydrocarbons of the present invention.

FIG. 4 is a view for illustrating the fourth embodiment of the method for producing monocyclic aromatic hydrocarbons of the present invention. The method for producing monocyclic aromatic hydrocarbons of the present embodiment is also a method for producing monocyclic aromatic hydrocarbons having 6 to 8 carbon atoms from oil feedstock.

That is, the method for producing monocyclic aromatic hydrocarbons of the present embodiment may include the respective steps shown in FIG. 4.

(26) A cracking and reforming reaction step of bringing oil feedstock into contact with a catalyst for producing monocyclic aromatic hydrocarbons to cause a reaction and obtain a product containing monocyclic aromatic hydrocarbons having 6 to 8 carbon atoms and a heavy fraction having 9 or more carbon atoms

(27) A separation step of separating the product formed by the cracking and reforming reaction step into plural fractions

(28) A purification and recovery step of purifying and recovering monocyclic aromatic hydrocarbons separated by the separation step

(29) A first returning step of returning at least a portion of toluene obtained by the purification and recovery step to the cracking and reforming reaction step

(30) A second returning step of returning the heavy fraction having 9 or more carbon atoms separated from the product formed by the cracking and reforming reaction step to the cracking and reforming reaction step

(31) A dilution step of adding a diluent to the heavy fraction having 9 or more carbon atoms separated from the product formed by the cracking and reforming reaction step

(32) A hydrogenation reaction step of hydrogenating a mixture obtained by the dilution step

(33) A recycle step of returning hydrogenation products of the mixture obtained by the hydrogenation reaction step to the cracking and reforming reaction step

(34) A diluent recovery step of separating and removing the diluent from the hydrogenation products of the mixture obtained by the hydrogenation reaction step and recovering the diluent to reuse it as a diluent of the dilution step

(35) A hydrogen recovery step of recovering hydrogen produced as a by-product by the cracking and reforming reaction step, from a gas component separated by the separation step

(36) A hydrogen supply step of supplying the hydrogen recovered by the hydrogen recovery step to the hydrogenation reaction step Among the steps (26) to (36), the steps (26), (28), (29), (31), (32), (33), and (34) are steps included in a seventh embodiment, and the steps (27), (30), (35), and (36) are optional steps.

The (26) cracking and reforming reaction step can be performed in the same manner as the (1) cracking and reforming reaction step in the first embodiment.

The (27) separation step can be performed in the same manner as the (2) separation step in the first embodiment.

The (28) purification and recovery step can be performed in the same manner as the (3) purification and recovery step in the first embodiment.

The (29) first returning step can be performed in the same manner as the (10) first returning step in the second embodiment. Moreover, a portion of the toluene obtained by the purification and recovery step may be supplied to the dilution step as a portion of a diluent.

The (30) second returning step can be performed in the same manner as the (20) second returning step in the third embodiment.

The (32) hydrogenation reaction step can be performed in the same manner as the (12) hydrogenation reaction step in the second embodiment. That is, the toluene to be returned to the cracking and reforming reaction step by the first returning step is supplied to a middle portion (a portion between an inlet and an outlet of the hydrogenation reactor) of the hydrogenation reactor used in the hydrogenation reaction step.

The (35) hydrogen recovery step can be performed in the same manner as the (24) hydrogen recovery step in the third embodiment.

The (36) hydrogen supply step can be performed in the same manner as the (25) hydrogen supply step in the third embodiment.

<Dilution Step>

In the (31) dilution step in the present embodiment, in the same manner as an example described for the (21) dilution step in the third embodiment, a diluent formed of a hydrocarbon other than toluene is added to the heavy fraction having 9 or more carbon atoms separated by the separation step such that the concentration of polycyclic aromatic hydrocarbons in a mixture of the heavy fraction having 9 or more carbon atoms and the diluent becomes lower than the concentration of polycyclic aromatic hydrocarbons in the heavy fraction. Moreover, as described above, a portion of the toluene obtained by the purification and recovery step may be used as a portion of the diluent, together with the diluent formed of a hydrocarbon other than toluene.

As the diluent which is used in the present embodiment and formed of a hydrocarbon other than toluene, the diluent recovered by the diluent recovery step which will be described later is reused. Here, at the time of start-up or in a case where the amount of the diluent is insufficient since it is not recovered in the diluent recovery step, a hydrocarbon is supplied from a storage tank or the like that is separately prepared.

Therefore, as a diluent, a diluent which is easily separated and recovered from the hydrogenation products by the diluent recovery step unlike the diluent described in the third embodiment, specifically, a diluent which is easily separated from hydrides of polycyclic aromatic hydrocarbons (particularly, naphthenobenzene) by a distillation operation is used. As such a diluent, a hydrocarbon that is not easily hydrogenated is used as in the third embodiment. Accordingly, the diluent does not contain polycyclic aromatic hydrocarbons, which have a boiling point higher than that of naphthenobenzene and are easily hydrogenated, as a main component. The diluent of the present embodiment can be recycled over and over in the hydrogenation reaction step, the diluent recovery step, and the dilution step as shown in FIG. 4. Consequently, sometimes the amount of the diluent may decrease since a portion of the diluent is not recovered by the diluent recovery step or the like, or sometimes the amount of the diluent may increase since a portion of the heavy fraction undergoes cracking or the like and is recovered as a diluent by the diluent recovery step.

Thus, if necessary, the amount of the diluent to be recycled needs to be controlled. However, in any case, it is preferable to use a material that is not easily hydrogenated or cracked by the hydrogenation reaction step.

Therefore, as such a hydrocarbon, for example, a hydrocarbon which is produced by the hydrogenation reaction step and has a boiling point lower than that of t-decalin (t-decahydronaphthalene) having a boiling point of 185° C. is preferably used. That is, naphthene, paraffin, or a monocyclic aromatic compound which is easily separated from polycyclic aromatic hydrocarbons or naphthenobenzene by the distillation operation and is not easily hydrogenated is preferably used as the diluent.

The dilution step of the present embodiment is the same as the dilution step of the third embodiment, except that the present dilution step mainly uses the diluent described above. That is, the concentration of polycyclic aromatic hydrocarbons of the mixture formed by being diluted with the diluent is the same as the concentration obtained by the dilution step of the third embodiment. In addition, regarding the dilution ratio obtained by the diluent, that is, the mass ratio (mixing ratio) between the heavy fraction and the diluent, since the present embodiment uses a diluent that basically does not contain polycyclic aromatic hydrocarbons, the amount of the diluent to be added can be reduced, compared to the amount in the mass ratio of the third embodiment (for example, heavy fraction:diluent=20:80 to 90:10).

<Diluent Recovery Step>

In the diluent recovery step, the diluent is separated and removed from the hydrogenation products of the mixture obtained by the hydrogenation reaction step and recovered. The recovered diluent is reused as the diluent to be added to the heavy fraction having 9 or more carbon atoms in the dilution step. The diluent recovered in this step is only a diluent formed of a hydrocarbon other than toluene. When a portion of the toluene obtained by the purification and recovery step is concurrently used as a diluent, the toluene is returned to the cracking and reforming reaction step without being recovered.

As the method of separating and removing the diluent from the hydrogenation products of the mixture, the distillation operation is preferably employed as described above. That is, in this diluent recovery step, the products are separated into, for example, components having a boiling point lower than 185° C. and components having a boiling point higher than 185° C. by a distillation tower, and accordingly, for example, the components having a boiling point lower than 185° C. can be separated from the components having a boiling point higher than 185° C. Consequently, by cooling and condensing the separated components having a boiling point lower than 185° C., that is, the diluent component, a diluent can be regenerated. Here, since the components having a boiling point lower than 185° C. also contain toluene, the toluene is returned to the cracking and reforming reaction step by the recycle step without being separated and recovered.

For example, when the respective components are separated by a distillation tower, the hydrogenation products are not simply separated into the components having a boiling point lower than 185° C. and the components having a boiling point higher than 185° C. From the components having a boiling point lower than 185° C., a component (toluene) having a 10 vol % distillation temperature of 85° C. or higher and a 90 vol % distillation temperature of 140° C. or lower is separated. In addition, components except for the component (toluene) which has a boiling point lower than 185° C. and has a 10 vol % distillation temperature of 85° C. or higher and a 90 vol % distillation temperature of 140° C. or lower are condensed by cooling and returned to the dilution step as a diluent. Alternatively, toluene is separated from the components which have already been separated and have a boiling point lower than 185° C., and a component other than the toluene is recovered and returned to the dilution step as a diluent. The diluent separated and recovered in this manner is sent to the dilution step and added to the heavy fraction to form a mixture, and the mixture is then recycled in the hydrogenation reaction step, the diluent recovery step, and the dilution step in this order.

<Recycle Step>

Unlike the (23) recycle step in the third embodiment, in the (33) recycle step, the entire hydrogenation products of the mixture obtained by the hydrogenation reaction step are not directly returned to the cracking and reforming reaction step. Instead, the fractions (fraction containing toluene) from which a diluent has been separated by the diluent recovery step are mixed with oil feedstock or separated returned to the cracking and reforming reaction step by being mixed with oil feedstock or separately returned to the cracking and reforming reaction step.

Since the method for producing monocyclic aromatic hydrocarbons of the present embodiment also includes the hydrogenation reaction step and the recycle step, monocyclic aromatic hydrocarbons having 6 to 8 carbon atoms can be produced at a high yield from the oil feedstock containing polycyclic aromatic hydrocarbons.

Moreover, since the method includes the dilution step, it is possible to suppress polycyclic aromatic hydrocarbons from generating excess heat in the hydrogenation reaction step and to avoid the extensive increase in the cost of equipment of the hydrogenation reactor.

In addition, the method includes the diluent recovery step of separating and removing the diluent from hydrogenation products of the mixture and recovering the diluent to reuse it. Therefore, due to the recycling of the diluent, a step of continuously supplying a new diluent becomes unnecessary, and the operation conditions can be simplified.

In the present embodiment, at least a portion of the toluene obtained by the purification and recovery step is supplied to the middle portion of the hydrogenation reactor used in the hydrogenation reaction step, as in the second embodiment. Accordingly, since the toluene is caused to function as a coolant (quenching agent), heat generated by the hydrogenation of polycyclic aromatic hydrocarbons in the hydrogenation reaction step can be reduced, whereby the hydrogenation reaction can be sufficiently performed to an appropriate degree even in a generally used conventional hydrogenation reactor.

Moreover, the toluene is returned to the cracking and reforming reaction step through the recycle step without being hydrogenated by the hydrogenation reaction step. Therefore, by causing a reaction such as disproportionation of toluene in the hydrogenation reaction step, a large amount of benzene or xylene can be selectively produced at a yield higher than that of toluene.

[Other Embodiments]

The present invention is not limited to the above embodiments and can be modified in various manners within a range that does not depart from the gist of the present invention.

For example, as the hydrogen used in the hydrogenation reaction step, hydrogen obtained by known hydrogen production method may be used instead of the hydrogen which is produced as a by-product by the cracking and reforming reaction step. Moreover, the hydrogen produced as a by-product by other catalytic cracking methods may be used.

In addition, the above embodiments may include a heavy fraction discharge step of extracting a portion of the heavy fraction having 9 or more carbon atoms, which is obtained from the fraction separated by the separation step, in a certain amount and discharging the portion outside the system.

EXAMPLES

Hereinafter, the present invention will be described in more detail based on examples and comparative examples, but the present invention is not limited to these examples.

Reference Example 1

As described below, production of benzene and xylene in the cracking and reforming reaction step by causing a disproportionation reaction of toluene was confirmed.

Toluene (100 mass %) was used as oil feedstock and supplied to the cracking and reforming reaction step described in the first embodiment. That is, toluene was brought into contact and reacted with a catalyst for producing monocyclic aromatic hydrocarbons (a catalyst obtained by adding a binder to an MFI-type zeolite supporting 0.2 mass % of gallium and 0.7 mass % of phosphorus) in a fluidized bed reactor such that the toluene came into contact with the zeolite component contained in the catalyst for 7 seconds at a reaction temperature of 538° C. and a reaction pressure of 0.3 MPaG, thereby performing a cracking and reforming reaction. Thereafter, monocyclic aromatic hydrocarbons having 6 to 8 carbon atoms were recovered, and as a result, benzene and xylene (the sum of o-xylene, m-xylene, and p-xylene) were obtained almost in the same amount as shown below. Accordingly, it was confirmed that if the contact time is short, a disproportionation reaction generating benzene and xylene from toluene mainly occurs.

Before cracking and reforming reaction: toluene (100 mass %)

After cracking and reforming reaction (contact time of 7 seconds)

| | |
|---|---|
| Benzene | (18 mass %) |
| Toluene | (59 mass %) |
| m- and p-xylenes | (13 mass %) |
| o-xylene | (4 mass %) |
| (the sum of xylenes was 17 mass %) | | in an example in which the contact time of the cracking and reforming reaction was changed to 12 seconds, the amount of benzene produced was larger than that of xylene produced as shown below Before cracking and reforming reaction: toluene (100 mass %)

After cracking and reforming reaction (contact time of 12 seconds)

| | |
|---|---|
| Benzene | (29 mass %) |
| Toluene | (45 mass %) |
| m- and p-xylenes | (14 mass %) |
| o-xylene | (4 mass %) |
| (the sum of xylenes was 18 mass %) | |

Accordingly, it was confirmed that when the contact time is lengthened, a dealkylation reaction proceeds in accordance with a disproportionation reaction.

From the above results, it was confirmed that by generating benzene and xylene from the toluene returned by the first returning step and by controlling the contact time in the cracking and reforming reaction step, a ratio between benzene and xylene produced from the toluene returned by the first returning step can be controlled to a certain degree.

In the following Example 1, based on the first embodiment shown in FIG. 1, monocyclic aromatic hydrocarbons were recovered through the separation step and the purification and recovery step from a product obtained by the cracking and reforming reaction step, and among the monocyclic aromatic hydrocarbons, a fraction mainly including toluene was returned to the cracking and reforming reaction step by the first returning step.

Example 1

The LCO (10 vol % distillation temperature of 215° C. and a 90 vol % distillation temperature of 318° C.) as oil feedstock shown in Table 1 was brought into contact and reacted with a catalyst for producing monocyclic aromatic hydrocarbons (a catalyst obtained by adding a binder to an MFI-type zeolite supporting 0.2 mass % of gallium and 0.7 mass % of phosphorus) in a fluidized bed reactor such that the LCO came into contact with the zeolite component contained in the catalyst for 12 seconds at a reaction temperature of 538° C. and a reaction pressure of 0.3 MPaG, thereby performing a cracking and reforming reaction. From the product, monocyclic aromatic hydrocarbons having 6 to 8 carbon atoms were recovered by gas-liquid separation and distillation. The amount of the recovered benzene, toluene, and xylene produced was measured using a 2-dimensional gas chromatography apparatus (manufactured by ZOEX Corporation, KT2006 GCXGC System), and as a result, the amount of the benzene, toluene, and xylene produced was 11 mass %, 17 mass %, and 7 mass % respectively. Subsequently, the recovered toluene was returned to the cracking and reforming reaction step and mixed with the oil feedstock such that the amount of the toluene became 17 parts by weight based on 100 parts by weight of the oil feedstock, and the cracking and reforming reaction was performed again under the above reaction conditions. As a result, benzene, toluene, and xylene were produced in an amount of 14 mass %, 21 mass %, and 9 mass % respectively.

TABLE 1

| Oil feedstock properties | | | | Analysis method |
|---|---|---|---|---|
| | Density at 15° C. | g/cm$^3$ | 0.9258 | JIS K 2249 |
| | Dynamic viscosity at 30° C. | mm$^2$/s | 2.817 | JIS K 2283 |
| Distillation properties | Initial distillation point | ° C. | 173 | JIS K 2254 |
| | 10 vol % distillation temperature | ° C. | 215 | |
| | 50 vol % distillation temperature | ° C. | 266 | |
| | 90 vol % distillation temperature | ° C. | 318 | |
| | End point | ° C. | 346 | |
| Composition analysis | Saturated compounds | vol % | 22.9 | JPI-5S-49 |
| | Olefinic compounds | vol % | 2.1 | |
| | Whole aromatics | vol % | 75 | |
| | Monocyclic aromatics | vol % | 27.6 | |
| | Bicyclic aromatics | vol % | 39.5 | |
| | Tricyclic or higher-cyclic aromatics | vol % | 7.9 | |

Comparative Example 1

A reaction was performed in the same manner as in Example 1, except that the steps performed after the step of returning the recovered toluene to the cracking and reforming reaction step were not performed. The amount of obtained benzene, toluene, and xylene produced was 11 mass %, 17 mass %, and 7 mass % respectively.

It was found that in Example 1, the amount of toluene was reduced, and the amount of benzene and xylene was increased, compared to Comparative example 1 in which the toluene was not returned.

Moreover, in Example 1, by repeating the step of returning toluene and performing a cracking and reforming reaction, almost all of the toluene disappeared finally, and benzene and xylene were produced in an amount of 20 mass % and 12 mass % respectively.

In the following Example 2, based on the second embodiment shown in FIG. 2, monocyclic aromatic hydrocarbons were recovered through the separation step and the purification and recovery step from the product obtained by the cracking and reforming reaction step, and a heavy fraction having 9 or more carbon atoms that was obtained by the separation step was returned to the hydrogenation reaction step by the second returning step. The recovered toluene fraction was sent to the hydrogenation reaction step by the first returning step, and the heavy fraction was subjected to hydrogenation by the hydrogenation reaction step and then returned again to the cracking and reforming reaction step by the recycle step.

Example 2

In the same manner as Example 1, the LCO (a 10 vol % distillation temperature of 215° C. and a 90 vol % distillation temperature of 318° C.) as oil feedstock shown in Table 1 was brought into contact and reacted with a catalyst for producing monocyclic aromatic hydrocarbons (a catalyst obtained by adding a binder to an MFI-type zeolite supporting 0.2 mass % of gallium and 0.7 mass % of phosphorus) in a fluidized bed reactor such that the LCO came into contact with the zeolite component contained in the catalyst for 12 seconds at a reaction temperature of 538° C. and a reaction pressure of 0.3 MPaG, thereby causing a cracking and reforming reaction. From the product, monocyclic aromatic hydrocarbons having 6 to 8 carbon atoms and a heavy fraction (heavy fraction) having 9 or more carbon atoms were recovered by gas-liquid separation and distillation. The amount of the recovered benzene, toluene, and xylene produced was measured using a 2-dimensional gas chromatography apparatus (manufactured by ZOEX Corporation, KT2006 GCXGC System), and as a result, the amount of the benzene, toluene, and xylene produced was 11 mass %, 17 mass %, and 7 mass % respectively. Moreover, the content of polycyclic aromatic hydrocarbons in the heavy fraction was measured to be 81 mass %.

Thereafter, by using a commercially available nickel-molybdenum catalyst, the above heavy fraction was subjected to hydrogenation under conditions of a hydrogenation reaction temperature of 350° C., a hydrogenation reaction pressure of 3 MPa, and an LHSV of 0.5 h$^{-1}$. Moreover, the recovered toluene was supplied (in an amount of 40 parts by weight based on 100 parts by weight of the heavy fraction) as a quenching agent to the hydrogenation reactor to suppress heating of the reactor. As a result of analyzing the obtained hydrogenation products, a conversion (calculated based on the amount of methylcyclohexane in the hydrogenation products) of toluene was confirmed to be 4%. Meanwhile, provided that the amount of the heavy fraction having undergone the hydrogenation treatment was 100 mass %, in the heavy fraction, the content of hydrocarbons having one aromatic ring was 65 mass %, and the content of hydrocarbons (polycyclic aromatic hydrocarbons) having 2 or more aromatic rings was 29 mass %.

Subsequently, the hydrogenation products were recycled in the cracking and reforming reaction step and mixed with the oil feedstock such that the amount of the hydrogenation products became 60 parts by weight based on 100 parts by weight of the oil feedstock, and the cracking and reforming reaction was performed again under the above reaction conditions. As a result, monocyclic aromatic hydrocarbons having 6 to 8 carbon atoms (benzene, toluene, and xylene) were obtained at a yield of 43 mass %. The amount of the obtained benzene, toluene, and xylene produced was 14 mass %, 20 mass %, and 9 mass % respectively.

It was found that in Example 2, the amount of polycyclic aromatic hydrocarbons produced increased, compared to Comparative example 1 in which the hydrogenation reaction step of the heavy fraction, quenching of the solution conducted using toluene, and the recycle step were not performed. It was also found that the proportion of toluene in the monocyclic aromatic hydrocarbons decreased, and the proportion of benzene and xylene increased. Moreover, it was understood that by repeating the steps of the second embodiment, the amount of toluene produced decreased since toluene turned into benzene and xylene, and accordingly, the amount of benzene and toluene produced increased.

In the following Example 3, based on the third embodiment shown in FIG. 3, monocyclic aromatic hydrocarbons were recovered through the separation step and the purification and recovery step from the product obtained by the cracking and reforming reaction step, and a heavy fraction having 9 or more carbon atoms obtained by the separation step was returned to the dilution step by the second returning step. Thereafter, the recovered toluene fraction was sent as a diluent to the dilution step by the first returning step and mixed with the heavy fraction having 9 or more carbon atoms, and the mixed fraction was subjected to hydrogenation by the hydrogenation reaction step and then returned to the cracking and reforming reaction step by the recycle step.

Example 3

In the same manner as Example 1, LCO (a 10 vol % distillation temperature of 215° C. and a 90 vol % distillation temperature of 318° C.) as oil feedstock shown in Table 1 was brought into contact and reacted with a catalyst for producing monocyclic aromatic hydrocarbons (a catalyst obtained by adding a binder to an MFI-type zeolite supporting 0.2 mass % of gallium and 0.7 mass % of phosphorus) in a fluidized bed reactor such that the LCO came into contact with the zeolite component contained in the catalyst for 12 seconds at a reaction temperature of 538° C. and a reaction pressure of 0.3 MPaG, thereby performing a cracking and reforming reaction. From the product, monocyclic aromatic hydrocarbons having 6 to 8 carbon atoms and a heavy fraction (heavy fraction) having 9 or more carbon atoms were recovered by gas-liquid separation and distillation. The amount of the recovered benzene, toluene, and xylene produced was measured using a 2-dimensional gas chromatography apparatus (manufactured by ZOEX Corporation, KT2006 GCXGC System), and as a result, the amount of the benzene, toluene, and xylene produced was 11 mass %, 17 mass %, and 7 mass % respectively. Moreover, the content of polycyclic aromatic hydrocarbons in the heavy fraction was confirmed to be 81 mass %.

Thereafter, the recovered toluene was mixed with the above heavy fraction, in an amount of 40 parts by weight based on 100 parts of the heavy fraction, and by using a commercially available nickel-molybdenum catalyst, the mixed fraction was subjected to hydrogenation under conditions of a hydrogenation reaction temperature of 350° C., a hydrogenation reaction pressure of 3 MPa, and an LHSV of 0.5 h$^{-1}$. As a result of analyzing the obtained hydrogenation products, a conversion (calculated based on the amount of methylcyclohexane in the hydrogenation products) of toluene was confirmed to be 5%. Meanwhile, provided that the amount of the heavy fraction having undergone the hydrogenation treatment was 100 mass %, in the heavy fraction, the content of hydrocarbons having one aromatic ring was 66 mass %, and the content of hydrocarbons (polycyclic aromatic hydrocarbons) having 2 or more aromatic rings was 28 mass %.

From these results, the toluene is not hydrogenated, and heavy hydrocarbons are hydrogenated by priority. Moreover, the fact that the toluene was not hydrogenated clearly shows that the diluent suppresses heating per unit volume. Meanwhile, the amount of polycyclic aromatic hydrocarbons in the heavy fraction has greatly decreased, and the heavy fraction is in a state preferable as oil to be supplied to the cracking and reforming reaction step.

Subsequently, the above hydrogenation products were recycled in the cracking and reforming reaction step and mixed with the oil feedstock, in an amount of 60 parts by weight based on 100 parts by weight of the oil feedstock, and the cracking and reforming reaction was performed again under the above reaction conditions. As a result, monocyclic aromatic hydrocarbons (benzene, toluene, and xylene) having 6 to 8 carbon atoms were obtained at a yield of 44 mass %. The amount of the obtained benzene, toluene, and xylene produced was 15 mass %, 20 mass %, and 9 mass % respectively.

It was understood that in Example 3, the amount of monocyclic aromatic hydrocarbons produced increased, compared to Comparative example 1 in which the dilution step performed using toluene, the hydrogenation reaction step of the heavy fraction, and the recycle step were not performed. It was also understood that the proportion of toluene in monocyclic aromatic hydrocarbons decreased, and the proportion of benzene and xylene increased. Moreover, it was understood that by repeating the steps of the third embodiment, the amount of toluene produced decreased since toluene turned into benzene and xylene, and accordingly, the amount of benzene and toluene produced increased.

In the following Example 4, based on the fourth embodiment shown in FIG. 4, monocyclic aromatic hydrocarbons were recovered through the separation step and the purification and recovery step from the product obtained by the cracking and reforming reaction step, and a heavy fraction having 9 or more carbon atoms that is obtained by the separation step was sent to the hydrogenation reaction step through the dilution step. Thereafter, the recovered toluene fraction was sent to the hydrogenation reaction step by the first returning step, the heavy fraction was subjected to hydrogenation by the hydrogenation reaction step, and the hydrogenation products were returned to the cracking and reforming reaction step through the step of recovering the diluent and the recycle step.

Example 4

In the same manner as Example 3, the LCO (a 10 vol % distillation temperature of 215° C. and a 90 vol % distillation temperature of 318° C.) as oil feedstock shown in Table 1 was brought into contact and reacted with a catalyst for producing monocyclic aromatic hydrocarbons (a catalyst obtained by adding a binder to an MFI-type zeolite supporting 0.2 mass % of gallium and 0.7 mass % of phosphorus) in a fluidized bed reactor such that the LCO came into contact with the zeolite component contained in the catalyst for 12 seconds at a reaction temperature of 538° C. and a reaction pressure of 0.3 MPaG, thereby performing a cracking and reforming reaction. From the product, monocyclic aromatic hydrocarbons and a heavy fraction (heavy fraction) having 9 or more carbon atoms were recovered by gas-liquid separation and distillation. The amount of the recovered benzene, toluene, and xylene produced was measured using a 2-dimensional gas chromatography apparatus (manufactured by ZOEX Corporation, KT2006 GCXGC System), and as a result, the amount of the benzene, toluene, and xylene produced was 11 mass %, 17 mass %, and 7 mass % respectively. Moreover, the content of polycyclic aromatic hydrocarbons in the heavy fraction was measured to be 81 mass %.

Thereafter, trimethylbenzene as a diluent was mixed with the above heavy fraction, in an amount of 60 parts by weight based on 100 parts by weight of the heavy fraction, and by using a commercially available nickel-molybdenum catalyst, the mixed oil was subjected to hydrogenation treatment under conditions of a hydrogenation reaction temperature of 350° C., a hydrogenation reaction pressure of 3 MPa, and an LHSV of 0.5 h$^{-1}$. Moreover, the recovered toluene was supplied (in an amount of 40 parts by weight based on 100 parts by weight of the heavy fraction) as a quenching agent to the hydrogenation reactor to suppress heating of the reactor. As a result of analyzing the obtained hydrogenation products, a conversion (calculated based on the amount of methylcyclohexane in the hydrogenation products) of toluene was confirmed to be 5%. In addition, trimethylbenzene mixed as a diluent was not hydrogenated. Meanwhile, provided that the amount of the heavy fraction having undergone the hydrogenation treatment was 100 mass %, in the heavy fraction, the content of hydrocarbons having one aromatic ring was 79 mass %, and the content of hydrocarbons (polycyclic aromatic hydrocarbons) having 2 or more aromatic rings was 14 mass %.

Subsequently, by distillation, the hydrogenation products were separated into a fraction containing toluene and methylcyclohexane, a fraction (trimethylenzene fraction) mainly containing trimethylbenzene, and a heavy fraction, and hydrogenation products from which only the trimethylbenzene fraction was removed were prepared.

It was confirmed that the trimethylbenzene added as a diluent was hardly hydrogenated, and could be repeatedly used as a diluent by being recovered.

The fact that hydrogenation has not occurred clearly shows that the diluent suppresses heating per unit volume. It was also understood that in this example, the toluene was hardly hydrogenated and exerted an effect as a quenching agent. Meanwhile, it could be confirmed that the amount of bicyclic aromatic hydrocarbons of the heavy fraction greatly decreased, and the heavy fraction was in a state preferable as oil to be supplied to the cracking and reforming reaction step. This is because polycyclic aromatic hydrocarbons are more easily hydrogenated compared to monocyclic aromatic hydrocarbons, as in Example 3.

Then the hydrogenation products from which the trimethylbenzene fraction was removed was mixed with oil feedstock, in an amount of 55 parts by weight based on 100 parts by weight of the oil feedstock, and the cracking and reforming reaction was performed again under the above reaction conditions. As a result, monocyclic aromatic hydrocarbons (benzene, toluene, and xylene) were obtained at a yield of 43 mass %. The amount of the obtained benzene, toluene, and xylene produced was 15 mass %, 20 mass %, and 8 mass % respectively.

It was understood that in Example 4, the amount of monocyclic aromatic hydrocarbons produced increased, compared to Comparative example 1 in which the dilution step, quenching of the solution conducted using toluene, the hydrogenation reaction step, the diluent recovery step, and the recycle step were not performed. It was also understood that the proportion of toluene in the monocyclic aromatic hydrocarbons decreased, and the proportion of benzene and xylene increased. By repeating these reactions, the amount of toluene produced decreased since the toluene turned into benzene and xylene, and accordingly, the amount of benzene and toluene produced increased.

The invention claimed is:

1. A method for producing monocyclic aromatic hydrocarbons having 6 to 8 carbon atoms from oil feedstock having a 10 vol % distillation temperature of 140° C. or higher and a 90 vol % distillation temperature of 380° C. or lower, comprising:
   a cracking and reforming reaction step of bringing the oil feedstock into contact with a catalyst for producing monocyclic aromatic hydrocarbons containing a crystalline aluminosilicate and partially hydrogenating a polycyclic aromatic hydrocarbon by a reaction in which hydrogen is transferred from a saturated hydrocarbon contained in the oil feedstock and used as a hydrogen-donating source to cause a reaction and obtain a product containing monocyclic aromatic hydrocarbons having 6 to 8 carbon atoms and a heavy fraction having 9 or more carbon atoms;
   a purification and recovery step of purifying and recovering the monocyclic aromatic hydrocarbons having 6 to 8 carbon atoms separated from the product formed by the cracking and reforming reaction step; and
   a first returning step of returning at least a portion of toluene obtained by the purification and recovery step to the cracking and reforming reaction step.

2. The method for producing monocyclic aromatic hydrocarbons according to claim 1, further comprising a second returning step of returning the heavy fraction having 9 or more carbon atoms separated from the product formed by the cracking and reforming reaction step to the cracking and reforming reaction step.

3. The method for producing monocyclic aromatic hydrocarbons according to claim 1, further comprising:
   a hydrogenation reaction step of hydrogenating the heavy fraction having 9 or more carbon atoms separated from the product formed by the cracking and reforming reaction step; and
   a recycle step of returning hydrogenation products of the heavy fraction obtained by the hydrogenation reaction step to the cracking and reforming reaction step.

4. The method for producing monocyclic aromatic hydrocarbons according to claim 3,
   wherein the first returning step is a step of supplying the toluene to a middle portion of a hydrogenation reactor used in the hydrogenation reaction step.

5. The method for producing monocyclic aromatic hydrocarbons according to claim 3, further comprising, between the cracking and reforming reaction step and the hydrogenation reaction step, a dilution step of adding a diluent formed of a hydrocarbon to the heavy fraction having 9 or more carbon atoms separated from the product formed by the cracking and reforming reaction step.

6. The method for producing monocyclic aromatic hydrocarbons according to claim 5,
   wherein as the diluent, at least a portion of toluene obtained by the purification and recovery step is used.

7. The method for producing monocyclic aromatic hydrocarbons according to claim 5, further comprising, after the hydrogenation reaction step, a diluent recovery step of separating and removing the diluent from the hydrogenation products obtained by the hydrogenation reaction step and recovering the diluent to reuse it as a diluent of the dilution step.

8. The method for producing monocyclic aromatic hydrocarbons according to claim 2, further comprising:
   a hydrogenation reaction step of hydrogenating the heavy fraction having 9 or more carbon atoms separated from the product formed by the cracking and reforming reaction step; and
   a recycle step of returning hydrogenation products of the heavy fraction obtained by the hydrogenation reaction step to the cracking and reforming reaction step.

9. The method for producing monocyclic aromatic hydrocarbons according to claim 8,
   wherein the first returning step is a step of supplying the toluene to a middle portion of a hydrogenation reactor used in the hydrogenation reaction step.

10. The method for producing monocyclic aromatic hydrocarbons according to claim 4, further comprising, between the cracking and reforming reaction step and the hydrogenation reaction step, a dilution step of adding a diluent formed of a hydrocarbon to the heavy fraction having 9 or more carbon atoms separated from the product formed by the cracking and reforming reaction step.

11. The method for producing monocyclic aromatic hydrocarbons according to claim 10,
   wherein as the diluent, at least a portion of toluene obtained by the purification and recovery step is used.

12. The method for producing monocyclic aromatic hydrocarbons according to claim 10, further comprising, after the hydrogenation reaction step, a diluent recovery step of separating and removing the diluent from the hydrogenation products obtained by the hydrogenation reaction step and recovering the diluent to reuse it as a diluent of the dilution step.

* * * * *